US009150862B2

(12) United States Patent
Smith et al.

(10) Patent No.: US 9,150,862 B2
(45) Date of Patent: Oct. 6, 2015

(54) SIRNA TARGETING VEGFA AND METHODS FOR TREATMENT IN VIVO

(71) Applicants: Anja Smith, Thronton, CO (US); Angela Reynolds, Littleton, CO (US); Jon E. Chatterton, Fort Worth, TX (US); Xinyu Zhang, Southlake, TX (US)

(72) Inventors: Anja Smith, Thronton, CO (US); Angela Reynolds, Littleton, CO (US); Jon E. Chatterton, Fort Worth, TX (US); Xinyu Zhang, Southlake, TX (US)

(73) Assignees: Thermo Fisher Scientific Inc., Waltham, MA (US); Arrowhead Research Corporation, Madison, WI (US)

( * ) Notice: Subject to any disclaimer, the term of this patent is extended or adjusted under 35 U.S.C. 154(b) by 0 days.

(21) Appl. No.: 14/010,749

(22) Filed: Aug. 27, 2013

(65) Prior Publication Data
US 2014/0031414 A1 Jan. 30, 2014

Related U.S. Application Data

(62) Division of application No. 13/190,797, filed on Jul. 26, 2011, now Pat. No. 8,546,349.

(60) Provisional application No. 61/368,385, filed on Jul. 28, 2010.

(51) Int. Cl.
*C07H 21/04* (2006.01)
*C12N 15/113* (2010.01)
*A61K 31/713* (2006.01)

(52) U.S. Cl.
CPC .......... *C12N 15/1136* (2013.01); *A61K 31/713* (2013.01); *C12N 2310/14* (2013.01)

(58) Field of Classification Search
CPC ........................ C12N 2310/14; C12N 15/1136
See application file for complete search history.

(56) References Cited

U.S. PATENT DOCUMENTS

| | | | |
|---|---|---|---|
| 5,830,879 A | 11/1998 | Isner | |
| 6,057,437 A | 5/2000 | Kamiya | |
| 6,150,092 A | 11/2000 | Uchida et al. | |
| 6,573,099 B2 | 6/2003 | Graham | |
| 7,345,027 B2 | 3/2008 | Tolentino et al. | |
| 2005/0255487 A1 | 11/2005 | Khvorova et al. | |
| 2007/0031844 A1 | 2/2007 | Khvorova et al. | |
| 2008/0027215 A1 | 1/2008 | Khvorova et al. | |
| 2008/0286866 A1 | 11/2008 | Quay et al. | |
| 2009/0209626 A1 | 8/2009 | Khvorova et al. | |
| 2010/0087508 A1 | 4/2010 | Bumcrot et al. | |
| 2010/0093085 A1 | 4/2010 | Yamada et al. | |
| 2010/0113307 A1 | 5/2010 | Khvorova et al. | |

FOREIGN PATENT DOCUMENTS

| | | |
|---|---|---|
| WO | 95/04142 A2 | 2/1995 |
| WO | 96/23065 A2 | 8/1996 |
| WO | 96/27006 A2 | 9/1996 |
| WO | 97/20925 A1 | 6/1997 |
| WO | 97/21808 A1 | 6/1997 |
| WO | 97/39120 A2 | 10/1997 |
| WO | 98/27425 A1 | 6/1998 |
| WO | 99/63975 A2 | 12/1999 |
| WO | 00/27414 A2 | 5/2000 |
| WO | 02/31141 A2 | 4/2002 |
| WO | 02/085308 A2 | 10/2002 |
| WO | 02/085309 A2 | 10/2002 |
| WO | 02/096927 A2 | 12/2002 |
| WO | 03/040366 A2 | 5/2003 |
| WO | 03/070910 A2 | 8/2003 |
| WO | 03/072704 A2 | 9/2003 |
| WO | 2004/009769 A2 | 1/2004 |
| WO | 2004/076639 A2 | 9/2004 |
| WO | 2005/028649 A1 | 3/2005 |
| WO | 2007/067981 A2 | 6/2007 |
| WO | 2008/045576 A2 | 4/2008 |
| WO | 2008/109362 A1 | 9/2008 |
| WO | 2009/045356 A2 | 4/2009 |
| WO | 2009/111658 A2 | 9/2009 |
| WO | 2010/065834 A1 | 6/2010 |

OTHER PUBLICATIONS

Kisielow Malgorzata et al.: "Isoform-specific knockdown and expression of adaptor protein ShcA using small interfering RNA", Biochemical Journal, vol. 363, No. 1, Apr. 1, 2002, pp. 1-5.
Extended European Search Report re EP 10013098.8, Dec. 20, 2011.
International Search Report and Written Opinion of the International Searching Authority. PCT/US11/45273. Mar. 7, 2012.
Australian Patent Examination Report No. 1, Australian Government, IP Australia, dated Nov. 24, 2013.
Shibata, M-A et al.: "Combination therapy with short interfering RNA vectors against VEGF-C and VEGF-A suppresses lymph node and lung metastasis in a mouse immunocompetent mammary cancer model," Cancer Gene Therapy, Appleton & Lange, vol. 15, No. 12, Jul. 1, 2008, pp. 776-786.
Extended European Search Report re EP 11 813 031.9, Jul. 14, 2014.

*Primary Examiner* — Brian Whiteman
(74) *Attorney, Agent, or Firm* — Dorf & Nelson LLP; Scott D. Locke, Esq.

(57) ABSTRACT

Vascular endothelial growth factor A (VEGFA) is a chemical signal produced by cells that stimulates the growth of new blood vessels, and overexpression of VEGFA can lead to undesirable physiological conditions. Through the identification of new siRNA and modifications that improve the silencing ability of these siRNA in vivo, therapeutic compositions and methods have been invented to address the problems associated with this overexpression.

5 Claims, 5 Drawing Sheets

SEQUENCE LISTING

```
<160> NUMBER OF SEQ ID NOS: 95

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
uacuaaaucu cucuccuuu                                                    19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
aaaggagaga gauuuagua                                                    19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
acagaacgau cgauacaga                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
ucuguaucga ucguucugu                                                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
cgacagaaca guccuuaau                                                    19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
auuaaggacu guucugucg                                                    19

<210> SEQ ID NO 7
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 7
gaagagacac auuguugga                                                    19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
uccaacaaug ugucucuuc                                                    19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
gucacuagcu uaucuugaa                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
uucaagauaa gcuagugac                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
cagcacacau uccuuugaa                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
uucaaaggaa ugugugcug                                                    19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
ggagaccacu ggcagaugu                                                    19
```

```
<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
acaucugcca guggucucc                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic

<400> SEQUENCE: 15
gcucggugcu ggaauuuga                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
ucaaauucca gcaccgagc                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17
gaaagacaga ucacaggua                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
uaccugugau cugucuuuc                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
ccagaaaccu gaaaugaag                                                    19

<210> SEQ ID NO 20
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 20
cuucauuuca gguuucugg                                                  19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
gagaagagac acauuguug                                                  19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
caacaaugug ucucuucuc                                                  19

<210> SEQ ID NO 23
<211> LENGTH: 19
<212> TYPE: RNA
<213> ORGANISM: Artificial Sequence
<220> FEATURE:
<223> OTHER INFORMATION: Synthetic

<400> SEQUENCE: 23
cgacaaagaa auacagaua                                                  19

<210> SEQ ID NO 24
<211> LENGTH: 19
<212> TYPE: RNA
<213> ORGANISM: Artificial Sequence
<220> FEATURE:
<223> OTHER INFORMATION: Synthetic

<400> SEQUENCE: 24
uaucuguauu ucuuugucg                                                  19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25
gggcaaauau gacccaguu                                                  19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
aacuggguca uauuugccc                                                  19

<210> SEQ ID NO 27
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 27
gaagagaaga gacacauug                                              19

<210> SEQ ID NO 28
<211> LENGTH: 19
<212> TYPE: RNA
<213> ORGANISM: Artificial Sequence
<220> FEATURE:
<223> OTHER INFORMATION: Synthetic

<400> SEQUENCE: 28
caaugugucu cuucucuuc                                              19

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
gaaaccagca gaaagagga                                              19

<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
uccucuuucu gcugguuuc                                              19

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
gaucacaggu acagggaug                                              19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
caucccugua ccugugauc                                              19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
```
ggaaagaggu agcaagagc                                                 19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
gcucuugcua ccucuuucc                                                 19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
gagaugagcu uccuacagc                                                 19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
gcuguaggaa gcucaucuc                                                 19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
gaucaaaccu caccaaggc                                                 19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
gccuugguga gguuugauc                                                 19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
caacaaaugu gaaugcaga                                                 19

<210> SEQ ID NO 40
<211> LENGTH: 19
<212> TYPE: RNA

```
<213> ORGANISM: Artificial Sequence
<220> FEATURE:
<223> OTHER INFORMATION: Synthetic

<400> SEQUENCE: 40
ucugcauuca cauuuguug                                                  19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
aaaugaagga agaggagac                                                  19

<210> SEQ ID NO 42
<211> LENGTH: 19
<212> TYPE: RNA
<213> ORGANISM: Artificial Sequence
<220> FEATURE:
<223> OTHER INFORMATION: Synthetic

<400> SEQUENCE: 42
gucuccucuu ccuucauuu                                                  19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
aaugcagacc aaagaaaga                                                  19

<210> SEQ ID NO 44
<211> LENGTH: 19
<212> TYPE: RNA
<213> ORGANISM: Artificial Sequence
<220> FEATURE:
<223> OTHER INFORMATION: Synthetic

<400> SEQUENCE: 44
ucuuucuuug gucugcauu                                                  19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
acauaggaga gaugagcuu                                                  19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
aagcucaucu cuccuaugu                                                  19
```

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
acgacaaaga aauacagau                                                    19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48
aucuguauuu cuuugucgu                                                    19

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
agacacaccc acccacaua                                                    19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50 uauggggug ggugugucu                                                     19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
agacauugcu auucuguuu                                                    19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
aaacagaaua gcaaugucu                                                    19

<210> SEQ ID NO 53
<211> LENGTH: 19
<212> TYPE: RNA
<213> ORGANISM: Artificial Sequence
<220> FEATURE:

```
<223> OTHER INFORMATION: Synthetic

<400> SEQUENCE: 53
agagaaaaga gaaaguguu                                                    19

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
aacacuuucu cuuuucucu                                                    19

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
agcacacauu ccuuugaaa                                                    19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
uuucaaagga augugugcu                                                    19

<210> SEQ ID NO 57
<211> LENGTH: 19
<212> TYPE: RNA
<213> ORGANISM: Artificial Sequence
<220> FEATURE:
<223> OTHER INFORMATION: Synthetic

<400> SEQUENCE: 57
caaaugugaa ugcagacca                                                    19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
uggucugcau ucacauuug                                                    19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
cacacauucc uuugaaaua                                                    19
```

```
<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
uauuucaaag gaaugugug                                                19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
cagaacaguc cuuaaucca                                                19

<210> SEQ ID NO 62
<211> LENGTH: 19
<212> TYPE: RNA
<213> ORGANISM: Artificial Sequence
<220> FEATURE:
<223> OTHER INFORMATION: Synthetic

<400> SEQUENCE: 62
uggauuaagg acuguucug                                                19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
cagagaaaag agaaagugu                                                19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
acacuuucuc uuucucug                                                 19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65
ccagcacaua ggagagaug                                                19

<210> SEQ ID NO 66
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 66
caucucuccu augugcugg                                                    19

<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
cgagauauuc cguaguaca                                                    19

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68
uguacuacgg aauaucucg                                                    19

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69
cuacuguuua uccguaaua                                                    19

<210> SEQ ID NO 70
<211> LENGTH: 19
<212> TYPE: RNA
<213> ORGANISM: Artificial Sequence
<220> FEATURE:
<223> OTHER INFORMATION: Synthetic

<400> SEQUENCE: 70
uauuacggau aaacaguag                                                    19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
cugaaaugaa ggaagagga                                                    19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
uccucuuccu ucauuucag                                                    19

<210> SEQ ID NO 73
<211> LENGTH: 19
```

-continued

<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
gaaaugaagg aagaggaga                                          19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
ucuccucuuc cuucauuuc                                          19

<210> SEQ ID NO 75
<211> LENGTH: 19
<212> TYPE: RNA
<213> ORGANISM: Artificial Sequence
<220> FEATURE:
<223> OTHER INFORMATION: Synthetic

<400> SEQUENCE: 75
gaacaguccu uaauccaga                                          19

<210> SEQ ID NO 76
<211> LENGTH: 19
<212> TYPE: RNA
<213> ORGANISM: Artificial Sequence
<220> FEATURE:
<223> OTHER INFORMATION: Synthetic

<400> SEQUENCE: 76
ucuggauuaa ggacuguuc                                          19

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77
gagagaugag cuuccuaca                                          19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
uguaggaagc ucaucucuc                                          19

<210> SEQ ID NO 79
<211> LENGTH: 19
<212> TYPE: RNA
<213> ORGANISM: Artificial Sequence
<220> FEATURE:
<223> OTHER INFORMATION: Synthetic

<400> SEQUENCE: 79
gagauauucc guaguacau                                                    19

<210> SEQ ID NO 80
<211> LENGTH: 19
<212> TYPE: RNA
<213> ORGANISM: Artificial Sequence
<220> FEATURE:
<223> OTHER INFORMATION: Synthetic

<400> SEQUENCE: 80
auguacuacg gaauaucuc                                                    19

<210> SEQ ID NO 81
<211> LENGTH: 19
<212> TYPE: RNA
<213> ORGANISM: Artificial Sequence
<220> FEATURE:
<223> OTHER INFORMATION: Synthetic

<400> SEQUENCE: 81
gaggcagaga aaagagaaa                                                    19

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82
uuucucuuuu cucugccuc                                                    19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
gauauuaaca ucacgucuu                                                    19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
aagacgugau guuaauauc                                                    19

<210> SEQ ID NO 85
<211> LENGTH: 19
<212> TYPE: RNA
<213> ORGANISM: Artificial Sequence
<220> FEATURE:
<223> OTHER INFORMATION: Synthetic

<400> SEQUENCE: 85
gcacacauuc cuuugaaau                                                    19

<210> SEQ ID NO 86
<211> LENGTH: 19
<212> TYPE: RNA
<213> ORGANISM: Artificial Sequence -continued
<220> FEATURE:
<223> OTHER INFORMATION: Synthetic

<400> SEQUENCE: 86
auuucaaagg aaugugugc                                                    19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
gcggaucaaa ccucaccaa                                                    19

<210> SEQ ID NO 88
<211> LENGTH: 19
<212> TYPE: RNA
<213> ORGANISM: Artificial Sequence
<220> FEATURE:
<223> OTHER INFORMATION: Synthetic

<400> SEQUENCE: 88
uuggugaggu uugauccgc                                                    19

<210> SEQ ID NO 89
<211> LENGTH: 21
<212> TYPE: RNA
<213> ORGANISM: Artificial Sequence
<220> FEATURE:
<223> OTHER INFORMATION: Synthetic

<400> SEQUENCE: 89
ugguuuacau gucgacuaau u                                                 21

<210> SEQ ID NO 90
<211> LENGTH: 19
<212> TYPE: RNA
<213> ORGANISM: Artificial Sequence
<220> FEATURE:
<223> OTHER INFORMATION: Synthetic
<221> NAME/KEY: misc_feature
<222> LOCATION: 1  2
<223> OTHER INFORMATION: 2' O methyl group

<400> SEQUENCE: 90
acagcaaauu ccaucgugu                                                    19

<210> SEQ ID NO 91
<211> LENGTH: 19
<212> TYPE: RNA
<213> ORGANISM: Artificial Sequence
<220> FEATURE:
<223> OTHER INFORMATION: Synthetic

<400> SEQUENCE: 91
agagauaaga gauagugua                                                    19

<210> SEQ ID NO 92
<211> LENGTH: 19
<212> TYPE: RNA
<213> ORGANISM: Artificial Sequence
<220> FEATURE:
<223> OTHER INFORMATION: Synthetic

<400> SEQUENCE: 92

```
ugguuaacau gucgacuaa                                                    19

<210> SEQ ID NO 93
<211> LENGTH: 21
<212> TYPE: RNA
<213> ORGANISM: Artificial Sequence
<220> FEATURE:
<223> OTHER INFORMATION: Synthetic

<400> SEQUENCE: 93
uuagucgaca uguaaaccau u                                                 21

<210> SEQ ID NO 94
<211> LENGTH: 19
<212> TYPE: RNA
<213> ORGANISM: Artificial Sequence
<220> FEATURE:
<223> OTHER INFORMATION: Synthetic

<400> SEQUENCE: 94
agagauaacu cauagugua                                                    19

<210> SEQ ID NO 95
<211> LENGTH: 21
<212> TYPE: RNA
<213> ORGANISM: Artificial Sequence
<220> FEATURE:
<223> OTHER INFORMATION: Synthetic

<400> SEQUENCE: 95
aacacuuuga guuuucucuu u                                                 21
```

SIRNA TARGETING VEGFA AND METHODS FOR TREATMENT IN VIVO

CROSS-REFERENCE TO RELATED APPLICATIONS

This application is a divisional of U.S. Ser. No. 13/190,797, filed Jul. 26, 2011, issued Oct. 1, 2013 as U.S. Pat. No. 8,546,349, and U.S. Ser. No. 13/190,797 claims the benefit of the filing date of U.S. Provisional Application Ser. No. 61/368,385, filed Jul. 28, 2010; the entire disclosures of both applications are incorporated by reference as if set forth fully herein.

FIELD OF INVENTION

The present invention relates to the use of siRNA.

BACKGROUND OF THE INVENTION

Angiogeneis is a physiological process that involves the growth of new blood vessels. An important part of this process is the production of vascular endothelial growth factor ("VEGF" or "VEGFA"), which is a chemical signal that is produced by cells and that stimulates the growth of new blood vessels.

The process is initiated when VEGFA is secreted by cells and binds to one or more cognate receptors such as the transmembrane protein kinase VEGFR1/FLT-1 and VEGFR2/FLK-1/KDR. After VEGFA binds to the transmembrane protein, a signal cascade is initiated that ultimately results in neovascularization.

Angiogeneis can be part of normal and vital body development and regulation. Unfortunately, it can also be associated with a number of undesirable conditions such as retinopathy, psoriasis, cancer, exudative age-related macular degeneration (ARMD), and rheumatoid arthritis. In these conditions, as well as in others, there are both high levels of VEGFA and concomitant increases in vascularization. Thus, the development of therapeutic strategies that focus on control of the production of VEGFA are being sought.

SUMMARY OF THE INVENTION

The present invention is directed to compositions and methods for the suppression of VEGFA expression, as well as to the treatment of conditions that are associated with the overexpression of VEGFA. Accordingly, the present invention provides kits, siRNAs and methods for introducing siRNA that suppress, in whole or in part, the production of VEGFA.

According to a first embodiment, the present invention provides a method for suppressing the expression of VEGFA. The method comprises administering in vivo (e.g., in a human) an siRNA that comprises a sequence that is a selected from the group consisting of: SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88 to an organism.

According to a second embodiment, the present invention provides a method for suppressing the expression of VEGFA. The method comprises administering in vitro an siRNA that comprises a sequence that is selected from the group consisting of: SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88.

According to a third embodiment, the present invention provides a method for suppressing expression of VEGFA. The method comprises administering an siRNA according to either of the first two embodiments, wherein the siRNA has one or more of the following modifications: 2'-O-alkyl (e.g., 2'-O-methyl) modifications of all C and U nucleotides within the sense strand as well as on the first two 5' nucleotides of the sense strand, 2' Fluoro modifications of all of the C and U nucleotides within the antisense strand and a 5' phosphorylation of the nucleotide at position one of the antisense strand. In some embodiments the siRNA has 2'-O-alkyl modifications on all C and U nucleotides within the sense strand and at least one 2'-O-alkyl modification on the antisense strand. In some embodiments the siRNA has one or more overhangs of one to six nucleotides. In some embodiments all of the aforementioned modifications are present, and only those modifications are present, thus, all G and A nucleotides, other than those located at positions 1 and 2 of the sense strand have 2'-OH groups.

According to a fourth embodiment, the present invention provides a method for suppressing expression of VEGFA. The method comprises administering an siRNA according to any of the first three embodiments, wherein the siRNA has one or more of the following modifications: a cholesterol moiety attached by a C5 linker, and mismatches at one or more of positions 6, 13 and 19 of the sense strand where the sense strand is 19 nucleotides long and the antisense strand is also 19 nucleotides in length (excluding overhangs). The positions on the sense strand are measured from the 5' end of the sense strand wherein the first 5' nucleotide of the sense strand is identified as the 5'-most nucleotide that is base-paired with a nucleotide on the antisense strand. As such, by this definition, 5' sense strand overhang nucleotides are not included in the counting scheme. In some of these embodiments there are no 5' overhangs. In some of the embodiments there are one or two 3' overhangs of 1 to 6 bases or there are no overhangs. In some embodiments, except for at positions 6, 13 and 19, within the duplex region, there is 100% complementarity.

According to a fifth embodiment, the present invention provides a pool of at least two siRNA selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86 and 88.

According to a sixth embodiment, the present invention provides a pharmaceutical composition comprising a therapeutically effective amount of one or more of the siRNAs disclosed herein.

According to a seventh embodiment, the present invention provides a pharmaceutical composition comprising a therapeutically effective amount of an siRNA, wherein the siRNA consists of: (a) an antisense strand that is nineteen to thirty-six bases in length and that comprises a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88; and (b) a sense strand that is nineteen to thirty-six bases in length, wherein the antisense strand and the sense strand form a duplex region of seventeen to thirty base pairs and within the duplex region there is at least 75% complementary. In the event that the duplex region of the siRNA is longer than 19 base pairs in length, additional (sense and antisense) sequences are added to the 3' end of the antisense strand and 5' end of the sense strand.

Through the use of the methods, siRNAs and pharmaceutical compositions described herein, one may efficiently and effectively silence VEGFA.

DETAILED DESCRIPTION

Definitions

Figure 1A:
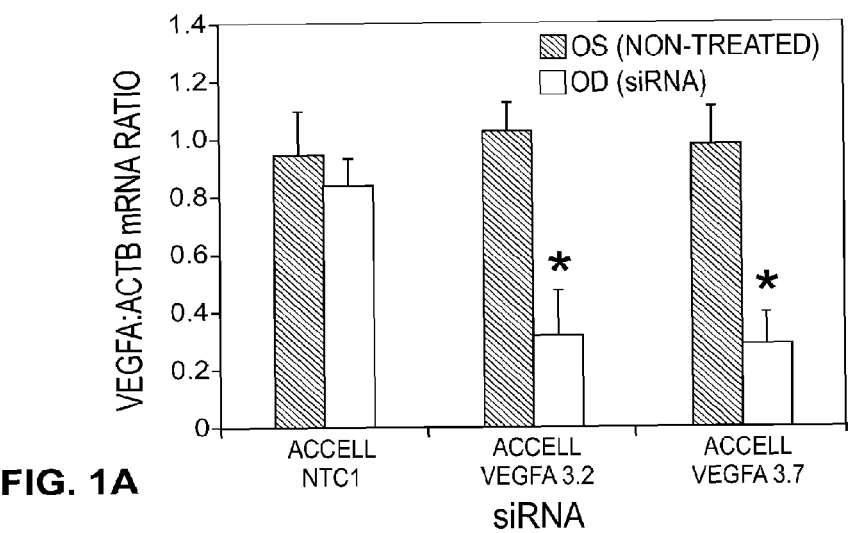
FIGS. 1A and B demonstrate the in vivo silencing activities of two VEGFA siRNAs modified as Accell molecules and delivered by intravitreal (IVT) injection in rats.

Unless stated otherwise or apparent from context, the following terms and phrases have the meanings provided below:

2' Modification

A 2' modification refers to a substitution of the hydroxyl group that is typically located at the 2' position of a ribose sugar within a ribonucleotide, with another moiety, e.g., an —O-alkyl group such as —O-methyl, —O-ethyl, —O-n-propyl, —O-isopropyl etc., or another group such as a fluoro group. Where —O-alkyl modifications are present, in some embodiments the same —O-alkyl group is present on all O-alkyl-modified nucleotides. Other types of 2' modifications are halogen groups, e.g., 2' Fluoro, or 2' bromo.

"Accell" siRNA

The term "Accell" refers to a preferred siRNA structure comprising the following: the sense strand is 19 nucleotides long and has: (1) 2'-O-methyl modifications on positions 1 and 2 (counting from the 5' terminus); (2) 2'-O-methyl modifications on all Cs and Us; and (3) cholesterol conjugated to the 3' terminus via a C5 linker. The antisense strand is 21 nucleotides in length, has a 5' phosphate modification, contains a 2' F modification on all Cs and Us, forms a 2 nucleotide overhang when paired with the sense strand, and contains phosphorthioate modification between (1) the two nucleotides of the overhang, and (2) between the 3' most nucleotide of the duplexed region and the first nucleotide of the overhang. In addition, Accell molecules contain mismatches at positions 6, 13, and 19 (counting from the 5' end of the sense strand). In all cases, these mismatches are generated by replacing the sense nucleotide with an alternative base. In this way, the antisense strand retains complete complementarity with the target molecule. For additional details, see US 2009/0209626 A1, the disclosure of which is incorporated by reference.

Complementary

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. In some embodiments, within a duplex region, there is at least 75% complementarity, at least 80% complementarity, at least 90% complementarity, at least 95% complementarity or 100% complementarity.

Conjugate Moiety

Conjugate moieties of the disclosure (also referred to simply as "conjugates") are moieties that are connected either directly or indirectly to a nucleotide and can target entry into a cell by a variety of means. For instance, conjugate moieties can be lipid in nature. As such, lipid based conjugate moieties can include cationic lipids, neutral lipids, sphingolipids, and fatty acids including stearic, oleic, elaidic, linoleic, linoleaidic, linolenic, and myristic acids. Alternatively, the conjugate moieties can be proteinaceous in nature including peptides that are membrane translocating (e.g., TAT, penetratin, MAP) or cationic (e.g., poly(lys), poly(arg), poly(his), poly (lys/arg/his), or protamine).

Alternatively, the conjugate moiety can be a small molecule that, for instance, targets a particular receptor or is capable of inserting itself into the membrane and being absorbed by endocytic pathways. Thus, small molecules based on adamantanes, polyaromatic hydrocarbons (e.g., napthalenes, phenanthrenes, or pyrenes), macrocyles, steroids, or other chemical scaffolds, are all potential conjugates for the disclosure.

In yet another alternative, conjugate moieties can be based on cationic polymers, such as polyethyleneimine, dendrimers, poly(alkylpyridinium) salts, or cationic albumin.

In some cases, the conjugate moieties are ligands for receptors or can associate with molecules that in turn associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g., capsids), toxins (e.g., bacterial toxins), and more. Also included are conjugates that are steroidal in nature e.g., cholesterol, cholestanol, cholanic acid, stigmasterol, pregnelone, progesterones, corticosterones, aldosterones, testosterones, estradiols, ergosterols, and more. Preferred conjugate moieties of the disclosure are cholesterol (CHOL), cholestanol (CHLN), cholanic acid (CHLA), stigmasterol (STIG), and ergosterol (ERGO).

In yet another embodiment, the molecules that target a particular receptor are modified to eliminate the possible loss of conjugated siRNAs to other sources. For instance, when cholesterol-conjugated siRNAs are placed in the presence of normal serum, a significant fraction of this material will associate with the albumin and/or other proteins in the serum, thus making the siRNA unavailable for e.g., interactions with LDLs. For this reason, the conjugate moieties of the disclosure can be modified in such a way that they continue to bind or associate with their intended target (e.g., LDLs) but have lesser affinities with unintended binding partners (e.g., serum albumin).

Duplex Region

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary.

Examples of sizes of duplex regions include but are not limited to 17-30 base pairs, 17-25 base pairs, 17-23 base pairs, 18-30 base pairs, 18-25 base pairs, 18-23 base pairs, 19-30 base pairs, 19-25 base pairs and 19-23 base pairs. A duplex region may be defined by the length of base pairs, as well as the degree of complementarity over that range.

Thus, when the duplex region is formed from two separate strands of nucleotides, the antisense strand and the sense strand, it is important to note that each strand may contain nucleotides that are part of the duplex and nucleotides that are not part of the duplex at either the 5' end or the 3' end. An siRNA may be designed such that on the antisense strand, all nucleotides that are complementary to a target are part of the duplex region, and thus have complementary nucleotides on the sense strand. However, the siRNA may be also be designed such that the antisense strand also contains nucleotides at either its 3' end and/or its 5' end that although not having complementary nucleotides on the sense strand, are part of a continuous stretch of nucleotides within the antisense strand that have complementary nucleotides on the target.

By way of example, a sense strand may contain 19 nucleotides and an antisense strand may contain 21 nucleotides. All but the two 3' most nucleotides of the antisense strand may be complementary to the 19 nucleotides on the sense strand, while the entire stretch of 21 nucleotides of the antisense strand may be complementary to a stretch of 21 nucleotides of the target. Alternatively, the two 3' most nucleotides of the antisense strand may be selected so as not to be complementary to a portion of the target, or selected randomly or to facilitate processing such that one or both might or might not be complementary to the two nucleotides of the target that are adjacent to the nucleotides to which the other 19 nucleotides of the antisense strand are complementary.

Additionally, in different embodiments, within a duplex region there may for example be no mismatches, one mismatch, two mismatches, three mismatches, four mismatches, or five mismatches.

Mismatch

The term "mismatch" includes a situation in which Watson-Crick base pairing does not take place between a nucleotide of a sense strand and a nucleotide of an antisense strand. Examples of mismatches include but are not limited to an A across from a G, a C across from an A, a U across from a C, a U across from a G, an A across from an A, a G across from a G, a C across from C, and a U across from a U.

Linker

A linker is a moiety that attaches two or more other moieties. Though not wishing to be limited by definitions or conventions, in this application the length of the linker is described by counting the number of atoms that represents the shortest distance between the atom that joins the conjugate moiety to the linker and the oxygen atom of the terminal phosphate moiety associated with the oligonucleotide through which the linker is attached to the oligonucleotide. For example, in embodiments where the conjugate moiety is joined to the linker via a carbamate linkage, the length of the linker is described as the number of atoms that represents the shortest distance between the nitrogen atom of the carbamate linkage and the oxygen atom of the phosphate linkage. In cases where ring structures are present, counting the atoms around the ring that represent the shortest path is preferred.

Non-limiting examples of structures of the conjugate-linker that may be used in the compositions and methods of the disclosure include but are not limited to linkers/linker chemistries that are based on β-amino-1,3-diols, β-amino-1,2-diols, hydroxyprolinols, ω-amino-alkanols, diethanolamines, β-hydroxy-1,3-diols, β-hydroxy-1,2-diols, β-thio-1,3-diols, β-thio-1,2-diols, β-carboxy-1,3-diols, β-carboxy-1,2-diols, ω-hydroxy-alkanols, ω-thio-alkanols, ω-carboxy-alkanols, functionalized oligoethylene glycols, allyl amine, acrylic acid, allyl alcohol, propargyl amine, and propargyl alcohol.

In some embodiments a linker not only provides a site of attachment to the conjugate moiety, but also provides functional sites for attachment to the support and for initiation of oligonucleotide synthesis. Preferably, these sites are hydroxyl groups; most preferably, they are a primary hydroxyl group and a secondary hydroxyl group, to allow them to be chemically distinguished during synthesis of the conjugate-modified solid support. One hydroxyl group, preferably the primary hydroxyl group, is protected with a protecting group that can be removed as the first step in the synthesis of the oligonucleotide, according to methods well understood by those of ordinary skill in the art. Preferably, this protecting group is chromophoric and can be used to estimate the amount of the conjugate moiety attached to the solid support; most preferably, the group is chosen from triphenylmethyl (Tr), monomethoxytriphenylmethyl (MMTr), dimethoxytriphenylmethyl (DMTr) and trimethoxytriphenylmethyl (TMTr). Another hydroxyl group, preferably a secondary hydroxyl group, is derivatized with a functionalized tether that can covalently react with a functional group on the solid synthesis support, according to methods well understood by those of ordinary skill in the art. Preferable tethers are, by way of example, dicarboxylic acids such as succinic, glutaric, terephthalic, oxalic, diglycolic, and hydroquinone-0,0'-diacetic. One of the carboxylic acid functionalities of the tether is reacted with the hydroxyl to provide an ester linkage that is cleavable using basic reagents (hydroxide, carbonate or amines), while the other carboxylic acid functionality is reacted with the synthesis support, usually through formation of an amide bond with an amine functionality on the support. The linker may also confer other desirable properties on the oligonucleotide conjugate: improved aqueous solubility, optimal distance of separation between the conjugate moiety and the oligonucleotide, flexibility (or lack thereof), specific orientation, branching, and others.

Preferably, the chemical bond between the linker and the conjugate moiety is a carbamate linkage; however, alternative chemistries are also within the scope of the disclosure. Examples of functional groups on linkers that form a chemical bond with a conjugate moiety include, but are not limited to, hydroxyl, amine, carboxylic acid, carboxylic acid halide, carboxylic acid active ester, carbonyl, chlorocarbonyl, imidazolylcarbonyl, thiol, maleimide, haloalkyl, sulfonyl, allyl and propargyl. Examples of chemical bonds that are formed between a linker and a conjugate include, but are not limited to, those based on carbamates, ethers, esters, amides, disulfides, thioethers, phosphodiesters, phosphorothioates, phorphorodithioate, sulfonamides, sulfonates, sulfones, sulfoxides, ureas, hydrazide, oxime, photolabile linkages, C—C bond forming groups such as Diels-Alder cyclo-addition pairs or ring-closing metathesis pairs, and Michael reaction pairs. In general, the conjugate moiety will have an appropriate functional group either naturally or chemically installed; the linker will then be synthesized with a functional group chosen to efficiently and stably react with the functional group on the conjugate moiety.

Linkers that have the same length, but are capable of associating with two or more conjugates, are also specifically contemplated.

In another embodiment, the linker may be a nucleoside derivative. The nucleoside may be, for example, a ribonucleoside, 2'-deoxyribonucleoside, or 2'-modified-2'-deoxyribonucleoside, such as 2'-O-methyl or 2'-fluoro. The nucleoside may be, for example, an arabinonucleoside or a 2'-modified arabinonucleoside. Using methods well known to those of ordinary skill in the art, purine and pyrimidine nucleosides may be modified at particular sites on the base to provide linkers and functional groups for attachment of conjugate moieties. For example, pyrimidine nucleosides, such as uridine and cytidine, may be modified at the 5-position of the uracil or cytosine base using mercuric acetate, a palladium catalyst, and an allylic reagent such as allylamine, allyl alcohol, or acrylic acid. Alternatively, 5-iodopyrimidines may be modified at the 5-position with a palladium catalyst and a propargylic reagent such as propargyl amine, propargyl alcohol or propargylic acid. Alternatively, uridine may be modified at the 4-position through activation with triazole or a sulfonyl chloride and subsequent reaction with a diamine, amino alcohol or amino acid. Cytidine may be similarly modified at the 4-position by treatment with bisulfite and subsequent reaction with a diamine, amino alcohol or amino acid. Purines may be likewise modified at the 7, 8 or 9 positions using similar types of reaction sequences.

In preferred embodiments, the linker is from about 3 to about 9 atoms in length. Thus, the linker may be 3, 4, 5, 6, 7, 8, or 9 atoms in length. Preferably, the linker is 5, 6, 7 or 8 atoms in length. More preferably, the linker is 5 or 8 atoms in length. Most preferably the linker is a straight chain C5 linker i.e., there are 5 carbon atoms between the atom that joins the conjugate moiety to the linker and the oxygen atom of the terminal phosphate moiety associated with the oligonucleotide through which the linker is attached to the oligonucleotide. Thus, where the conjugate moiety is joined to a C5 linker via a carbamate linkage, there are 5 carbon atoms between the nitrogen atom of the carbamate linkage and the oxygen atom of the phosphate linkage.

In one preferred embodiment, the conjugate moiety is cholesterol and the linker is a C5 linker (a 5 carbon linker) attached to the cholesterol via a carbamate group, thus forming a Chol-C5 conjugate-linker. When attached via a phosphodiester linkage to the 5' and/or 3' terminus of a sense and/or antisense oligonucleotide of a duplex, the resulting conjugate-linker-oligonucleotide can have the structure:

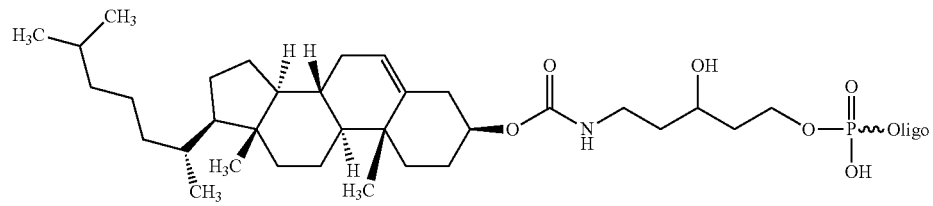

In another preferred embodiment, the conjugate moiety is cholesterol and the linker is a C3 linker attached to the cholesterol via a carbamate group, thus forming a Chol-C3 conjugate-linker. When attached via a phosphodiester linkage to the 5' and/or 3' terminus of a sense and/or antisense oligonucleotide, the resulting conjugate linker-oligonucleotide can have the structure:

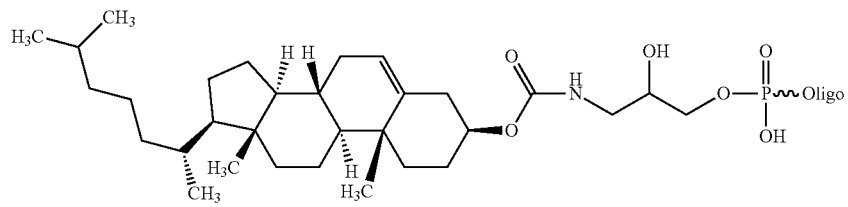

In another preferred embodiment, the conjugate moiety is cholesterol and the linker is a C8 linker (a 8 carbon linker) attached to the cholesterol via a carbamate group, thus forming a Chol-C8 conjugate-linker. When attached via a phosphodiester linkage to the 5' and/or 3' terminus of a sense and/or antisense oligonucleotide, the resulting conjugate-linker oligonucleotide can have the structure:

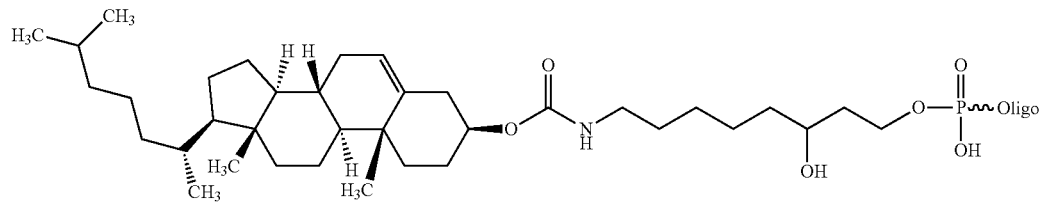

In another preferred embodiment, the conjugate moiety is cholesterol and the linker is a PRO linker (a 4 carbon linker) attached to the cholesterol via a carbamate group, thus forming a Chol-PRO conjugate-linker.

In another preferred embodiment, the conjugate moiety is cholesterol and the linker is a PIP linker (a 6 carbon linker) attached to the cholesterol via a carbamate group, thus forming a Chol-PIP conjugate-linker. When attached via a phosphodiester linkage to the 5' and/or 3' terminus of a sense and/or antisense oligonucleotide, the resulting conjugate-linker-oligonucleotide can have the structure:

In another preferred embodiment, the conjugate moiety is cholesterol and the linker is a C6-HP (also referred to as "HP6") linker (a 9 carbon linker) attached to the cholesterol via a carbamate group, thus forming a Chol-C6-HP conjugate-linker. When attached via a phosphodiester linkage to the 5' and/or 3' terminus of a sense and/or antisense oligonucleotide, the resulting conjugatelinker-oligonucleotide can have the structure:

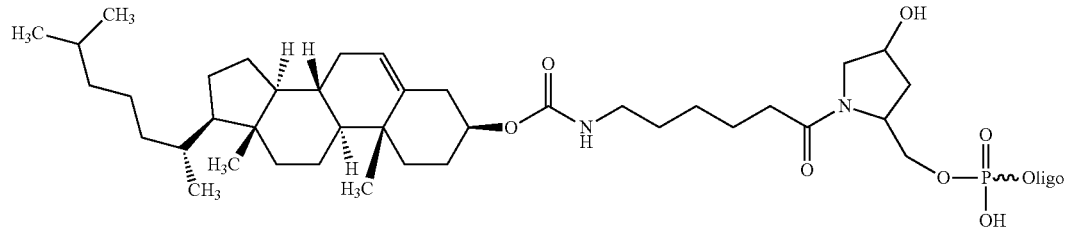

Nucleotide

Unless otherwise specified, the term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. In some embodiments, all nucleotides are selected from the group of modified or unmodified A, C, G or U.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

Further, the term nucleotide also includes those species that have a detectable label, such as for example a radioactive or fluorescent moiety, or mass label attached to the nucleotide.

Pharmaceutically Acceptable Carrier

The phrase "pharmaceutically acceptable carrier" means a pharmaceutically acceptable salt, solvent, suspending agent or vehicle for delivering a composition of the present disclosure to an organism such as an animal or human. The carrier may be liquid, semisolid or solid, and is often synonymously used with diluents, excipient, or salt. The phrase "pharmaceutically acceptable" means that any ingredient, excipient, carrier, diluent or component disclosed is one that is suitable for use with humans and/or animals without undue adverse side effects (such as toxicity, isolation and allergic response) commensurate with a reasonable benefit/risk ratio. See Remington's Pharmaceutical Science $16^{th}$ edition, Osol, A. Ed. (1980).

Ribonucleotide and Ribonucleic Acid

The term "ribonucleotide" and the phrase "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

Sense Strand/Antisense Strand

The phrase "sense strand" refers to a polynucleotide that comprises a sequence that is in whole or in part, the same as a target nucleic acid sequence such as messenger RNA or a sequence of DNA. The phrase "antisense strand" refers to a polynucleotide that comprises a sequence that is in whole or in part, the complement of a target nucleic acid sequence such as messenger RNA or a sequence of DNA.

When a sequence of an siRNA is provided, by convention, unless otherwise indicated it is of the sense strand, and the complementary antisense strand is implicit. In a duplex siRNA (formed from two separate strands) one strand may be the sense strand, and the other strand may be the antisense strand. If overhangs are present, the phrase "sense region" may refer to the nucleotide sequence portion of the sense strand other than overhang regions. Similarly, the phrase "antisense region" may refer to the nucleotide sequence portion of the antisense strand other than overhang regions. If the siRNA is a shRNA, there are not two separate strands, and the "sense region" is the portion of the duplex region that has a sequence that is in whole or in part the same as the target sequence, and the "antisense region" is the sequence of nucleotides that is in whole or in part complementary to the target sequence and to the sense region.

Examples of lengths of sense strands and antisense strands are 19-36 bases, 19-30 bases, 19-25 bases and 19-23 bases. These strand lengths include possible overhang regions.

siRNA

The term "siRNA" refers to small inhibitory RNA duplexes that induce the RNA interference (RNAi) pathway. As used herein, these molecules can vary in length (generally 17-30 base pairs plus overhangs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, and unless otherwise specified as well as single strands that can form hairpin structures comprising a duplex region, which is referred to as a shRNA.

siStable

The term "siStable" refers to a chemical modification pattern that is associated with a particular duplex. Specifically, siStable siRNA comprise the following structures: the sense strand is 19 nucleotides long and has (1) 2'-O-methyl modifications on positions 1 and 2 (counting from the 5' terminus), and (2) 2'-O-methyl modifications on all Cs and Us. The antisense strand is 21 nucleotides in length, has a 5' phosphate modification, contains a 2' F modification on all Cs and Us, forms a 2 nucleotide overhang when paired with the sense strand, and contains phosphorthioate modifications between (1) the two nucleotides of the overhang, and (2) between the 3' most nucleotide of the duplexed region and the first nucleotide of the overhang. For details, see US 2007/0269889 A1.

Target

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of identity and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

Therapeutically Effective Amount

A "therapeutically effective amount" of a composition containing a sequence that encodes a VEGFA-specific siRNA (i.e., an effective dosage), is an amount that inhibits expression of the polypeptide encoded by the VEGFA target gene by at least 10 percent. Higher percentages of inhibition, e.g., at least 15, at least 20, at least 30, at least 40, at least 50, at least 75, at least 85, at least 90 percent or higher may be preferred in certain embodiments. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the siRNA may be desired. When an inducible promoter is included in the construct encoding an siRNA, expression is assayed upon delivery to the subject of an appropriate dose of the substance used to induce expression.

Appropriate doses of a composition depend upon the potency of the molecule (the sequence encoding the siRNA) with respect to the expression or activity to be modulated. One or more of these molecules can be administered to an animal (e.g., a mammal such as a human or other primate, e.g., a chimpanzee, orangutan, ape, monkey etc., or dog, cat, horse, cow, rat, sheep, or mouse) to modulate expression or activity of one or more target polypeptides. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A therapeutically effective amount of a VEGFA-specific siRNA is useful for treating a condition, disease, or disorder associated with elevated expression of VEGFA, including, but not limited to, psoriasis, cancer, rheumatoid arthritis, ocular neovascularization, abnormal angiogenesis, retinal vascular permeability, retinal edema, diabetic retinopathy (particularly proliferative diabetic retinopathy), diabetic macular edema, exudative age-related macular degeneration, sequela associated with retinal ischemia, and posterior segment neovascularization.

Preferred Embodiments

The present invention will now be described in connection with preferred embodiments. These embodiments are presented in order to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

Furthermore, this disclosure is not a primer on compositions or methods for performing RNA interference. Basic concepts known to persons skilled in the art have not been set forth in detail.

According to a first embodiment, the present invention provides a method for decreasing expression of VEGFA, in vivo, comprising administering an siRNA to an organism, wherein the siRNA comprises a sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88.

The subject may be any organism that possesses an RNAi pathway, including, but not limited to a mammal, bird or reptile. Examples of mammals include, but are not limited to humans, monkeys, apes, chimpanzees, dogs, cats, mice and rats.

In addition, the duplex formed by the sense strand and the antisense strand can comprise at least one overhang, each overhang comprising at least one nucleotide. The overhang(s) can for example be located:
  at the 5' end of the sense strand;
  at the 3' end of the sense strand;
  at the 5' and 3' end of the sense strand;
  at the 5' end of the antisense strand;
  at the 3' end of the antisense strand;
  at the 5' and 3' end of the antisense strand;
  at the 5' end of the sense strand and the 5' end of the antisense strand; or
  at the 3' end of the sense strand and the 3' end of the antisense strand.

In some embodiments, the overhang is six or fewer nucleotides in length, in preferred embodiments, an overhang is present at the 3' end of the antisense strand, i.e., attached to the 3' most nucleotides of the antisense regions. More preferably, the overhang on the 3' end of the antisense strand is two nucleotides in length. The selection of the bases for nucleotides in the overhang may be made in an arbitrary manner i.e., the overhang nucleotides may or may not base pair with a target mRNA. For convenience and simplicity, a two nucleotide overhang is usually a UU overhang (although AA, GG, CC, AC, CA, AG, GA, GC, and CG di-nucleotide overhangs, and others, are also contemplated, see Vermeulen et al. (2005) RNA 11 (5): 674-682). Preferably, the linkage between the nucleotides of the overhang as well as the linkage between the terminal nucleotide of the duplex and the first nucleotide of the overhang are phosphorothioate linkages. In one particularly preferred embodiment, the antisense strand comprises a UU overhang located at the 3' end of the antisense strand with a phosphorothioate linkage linking the 3' terminal U to the second U nucleotide, and with a phosphorothioate linkage linking the second U nucleotide to the next nucleotide (in the 5' direction) in the antisense strand.

In some embodiments, the 5' end of the sense strand and/or the 3' end of the sense strand and/or the 5' end of the antisense strand and/or the 3' end of the antisense strand comprises a terminal phosphate. Preferably, a terminal phosphate is located at the 5' end of the antisense strand.

In some embodiments there are no modified nucleotides (i.e., the 2' position of each of the ribose sugars has an OH moiety). In other embodiments there are one or more than one chemical modifications. For example, there may be one or more or all of:

(1) 2'-O-alkyl modifications of positions 1 and 2 and all C nucleotides, and all U nucleotides of the sense strand (e.g., O-methyl, O-ethyl, O-n-propyl, O-isopropyl, etc.);

(2) a conjugate moiety wherein the conjugate moiety is comprised of, consists essentially of or consists of a linker and a conjugate moiety such as a cholesterol moiety and the linker is attached to the 3' position of the last nucleotide of the sense strand;

(3) 2' Fluoro modifications of all C and U nucleotides of the antisense strand or at least one 2'-O-alkyl modification on the antisense strand;

(4) phosphorylation at the 5' position of the first nucleotide of the antisense strand and all other nucleotides may in some embodiments be unmodified;

(5) one or more overhangs; and (6) one or more phosphorothioate modifications associated with the nucleotides of any overhang on either strand.

In some embodiments, where overhangs are present, 2'-O modifications may appear in the Cs and Us of the overhangs on the sense strand and 2'-fluoro modifications may appear in the Cs and Us of on the antisense strand. In other embodiments the 2'-O modifications and 2'-fluoro only appear within nucleotides in the duplex region. Additionally, in some embodiments it may be desirable to have all of the aforementioned 2' Cs and Us modified in each strand (either including or excluding in any overhang regions if present). However, in other embodiments it may be desirable to have fewer than all of the C and Us on each or either strand contain the aforementioned modifications. When fewer than all Cs and Us are modified, the total number of C and U modifications may be chosen by for example, an absolute number, for example 1-8 or 2-7 or 3-6 are modified or it may for example be defined in terms of the number that are not modified, e.g., all but 1, all but 2, all but 3, all but 4, all but 5, all but 6, all but 7, all but 8 of the Cs or Us are unmodified. In other embodiments, it may be preferable to omit a 2' modification at one or more specific positions, e.g., at one or more of positions 1, 2, 3, 4, 5, 6, 7, 8, 9, 10, 11, 12, 13, 14, 15, 16, 17, 18, and if present, 19, 20, 21, 22, 23, 24, 25, 26, 27, 28, 29 or 30. As a person of ordinary skill in the art will recognize preferably each strand contains at least one C or U nucleotide. Additionally, in some embodiments on the antisense strand it may be preferable to have 2' fluoro groups on 0-30 or 0-25 or 0-23 or 0-19 or 1-30 or 1-25 or 1-23 or 1-19 or 3-30 or 3-25 or 3-23 or 3-19 or 5-30 or 5-25 or 5-23 or 5-19 or 7-30 or 7-25 or 7-23 or 7-19 or 10-30 or 10-25 or 10-23 or 10-19 or 8-15 or 10-12 nucleotides. The modified nucleotides may all be pyrimidines, all be purines or be a combination of purines and pyrimidines. In some embodiments all nucleotides on the antisense strand have 2' fluoro groups and this strand may have at least one pyrimidine, at least one purine, all pyrimidines, all purines or a combination of purines and pyrimidines. Further in some embodiments the 2' fluoro groups are on any overhang nucleotides if present while in other embodiments, the overhang nucleotides do not include these modifications. Similarly, in some embodiments on the sense strand it may be preferable to have 2'-O-alkyl (e.g., 2'-O-methyl) groups on 0-30 or 0-25 or 0-23 or 0-19 or 1-30 or 1-25 or 1-23 or 1-19 or 3-30 or 3-25 or 3-23 or 3-19 or 5-30 or 5-25 or 5-23 or 5-19 or 7-30 or 7-25 or 7-23 or 7-19 or 10-30 or 10-25 or 10-23 or 10-19 or 8-15 or 10-12 nucleotides. The modified nucleotides may all be pyrimidines, all be purines or be a combination of purines and pyrimidines. In some embodiments all nucleotides on the sense strand have 2'-O-alkyl groups and this strand may have at least one pyrimidine, at least one purine, all pyrimidines, all purines or a combination of purines and pyrimidines. Further in some embodiments the 2'-O-alkyl groups are on any overhang nucleotides if present while in other embodiments, the overhang nucleotides do not include these modifications.

In embodiments that have at least one 2'-O-alkyl modification on the antisense strand, there may for example be, from one to ten, one to eight, one to six, one to five, one to four, one to three, or one to two modifications. In other embodiments, there may be exactly one, two, three, four, five, six, seven, eight, nine or ten such modifications. These at least one modifications may for example be located in a 3' antisense overhang region and/or at one or more of positions one to eight, one to seven, one to six, one to five, one to four, one to three, or one to two of the antisense strand as measured from the 5' end of that strand and within the duplex region.

By way of non-limiting examples, there may be a single 2'-O-alkyl modification (e.g., methyl) at any of positions 1, 2, 3, 4, 5, 6, 7 or 8 of the antisense strand. Alternatively, there may be a single 2'-O-alkyl modification in one of the two nucleotides in a UU overhang or in both of those nucleotides. Other combinations of 2'-O-alkyl modifications include but are not limited to at positions 1 and 2, 1 and 3, 1 and 4, 1 and 5, 1 and 6, 1 and 7, 1 and 8, 2 and 3, 2 and 4, 2 and 5, 2 and 6, 2 and 7, 2 and 8, 3 and 4, 3 and 5, 3 and 6, 3 and 7, 3 and 8, 4 and 5, 4 and 6, 4 and 7, 4 and 8, 5 and 6, 5 and 7, 5 and 8, 6 and 7, 6 and 8, 7 and 8, 1 and one of the two nucleotides in a UU overhang or in both of those nucleotides, 2 and one of the two nucleotides in a UU overhang or in both of those nucleotides, 3 and one of the two nucleotides in a UU overhang or in both of those nucleotides, 4 and one of the two nucleotides in a UU overhang or in both of those nucleotides, 5 and one of the two nucleotides in a UU overhang or in both of those nucleotides, 6 and one of the two nucleotides in a UU overhang or in both of those nucleotides, 7 and one of the two nucleotides in a UU overhang or in both of those nucleotides, or 8 and one of the two nucleotides in a UU overhang or in both of those nucleotides.

Furthermore, in some embodiments in which there is at least one 2'-O-alkyl modification present on the antisense strand the position is selected such that only A or G bases contain the modification, thereby allowing for all C and U bases to be modified with fluoro groups. In other embodiments, one or more C or U bases contain the 2'-O-alkyl modification. In those cases, the siRNA may be designed such that any C and U base that does not have a 2'-O-alkyl modification has a 2' fluoro modification.

In some embodiments, the siRNA contains a duplex region that is 17-30 base pairs long or 18-30 base pairs long or 19-30 base pairs long or 19-23 base pairs long or 19-21 base pairs long or 18-23 base pairs long. When a duplex region is 17 base pairs long and a 19-mer antisense sequence is provided, it may be that two bases at the 3' end of the antisense 19-mer form an overhang.

Within the duplex region there may be 100% complementarity or less than 100% complementarity, e.g., at least 80% complementarity, at least 85% complementarity, at least 90% complementarity, or at least 95% complementarity. In one embodiment, there is 100% complementarity except at sense strand position 6 or at position 13, or at position 19, or at positions 6 and 13 or at positions 13 and 19 or positions 6 and 19, or at positions 6, 13 and 19. In this example, at the designated position(s) there is a mismatch. Mismatches are introduced into the duplex by altering the identity of a nucleotide in the sense strand. In this way, the antisense strand retains 100% complementarity with the region of the target mRNA. Furthermore, as used herein, a position number within a strand refers to the location of that nucleotide relative to the first, i.e., 5' most, nucleotide of the duplex region. Thus, position 1 of the sense strand is the 5' most position of the sense strand, while position 1 of the antisense strand is the 5' most position of the antisense strand. Position 2 is the position immediately downstream (or 3') of position 1 of the respective strand.

As stated above, in some embodiments, a mismatch is introduced into the sense strand. In some cases, the nucleotides introduced at the positions of mismatch have the same identity or chemical nature as the nucleotide in the antisense strand that normally binds to that particular sense strand nucleotide. Thus, for example, if one has a double stranded molecule containing 19 nucleotides in the sense strand and 19 nucleotides in the antisense strand with no overhangs on either strand, if a mismatch is introduced at position 6 of the sense strand (counting from the 5' end of the strand), the nucleotide at that position of the sense strand does not pair in a Watson-Crick fashion with the nucleotide at position 14 of the antisense strand. Furthermore, if the nucleotide at position 14 of the antisense strand is e.g., a "C", then the mismatch would be achieved by introducing a "C" at position 6 of the sense strand. As a result of these changes, the nucleotide at position 6 of the sense strand no longer has identity with the corresponding nucleotide in the target region of e.g., the mRNA. However, the antisense nucleotide at e.g., position 14 would retain complementarity to the nucleotide on the target region.

The position of the conjugate-linker on the duplex oligonucleotide complex can vary with respect to the strand or strands that are conjugated (e.g., the sense strand, the antisense strand, or both the sense and antisense strands), the position or positions within the strand that are modified (i.e., the nucleotide positions within the strand or strands), and the position on the nucleotide(s) that are modified (e.g., the sugar, the base). Conjugate-linkers can be placed on the 5' and/or 3' terminus of one or more of the strands. For example, a conjugate-linker can be placed on the 5' end of the sense strand and/or the 3' end of the sense strand and/or the 3' end of the antisense strand. A conjugate-linker can be attached at the 5' and/or 3' end of a strand via a phosphodiester bond. In preferred embodiments, a conjugate-linker is attached to the one or both ends of the sense strand via a phosphodiester bond, more preferably to the 3' end of the sense strand.

A conjugate-linker can also be attached to internal positions of the sense strand and/or antisense strand. In addition, multiple positions on the nucleotides including the 5-position of uridine, 5-position of cytidine, 4-position of cytidine, 7-position of guanosine, 7-position of adenosine, 8-position of guanosine, 8-position of adenosine, 6-position of adenosine, 2'-position of ribose, 5'-position of ribose, and 3'-position of ribose, can be employed for attachment of the conjugate to the nucleic acid.

In another embodiment, the present invention provides a method of gene silencing, comprising introducing into a cell in vitro at least one siRNA that comprises a sequence that is selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88. The siRNA can be introduced by allowing passive uptake of siRNA, or through the use of a vector.

Any of the methods and kits disclosed herein can employ either unimolecular siRNAs, siRNAs comprised of two separate polynucleotide strands, or combinations thereof. Furthermore, any of the methods disclosed herein can be used in gene silencing using a variety of different protocols. In one non-limiting example, two or more siRNAs targeting the same gene can be administered simultaneously. As is the case with individual siRNAs, the two or more siRNA can be administered in a single dose or single transfection, in multiple doses, or as the case may be.

In one embodiment the invention provides the use of a compound that inhibits the expression and/or activity of a VEGFA gene for the manufacture of a medicament for treatment of a disorder associated with over-expression of VEGFA. The medicaments may, for example, be administered orally, parenterally (including subcutaneously, intramuscularly, or intravenously), rectally, transdermally, buccally, or nasally. The medicaments may comprise any one or more of the compounds described herein.

Interfering RNA may be delivered directly to the eye by ocular tissue injection such as periocular, conjunctival, sub-tenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

The present invention also provides pharmaceutical compositions that comprise an siRNA of the present invention in a pharmaceutically acceptable carrier. Thus, in another embodiment, the present invention is directed to a pharmaceutical composition comprising a therapeutically effective amount of an siRNA, wherein the siRNA consists of: (a) a sense strand and an antisense strand that form a duplex region, wherein the duplex region is 17-30 base pairs in length and comprises an antisense region that has a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86 and 88; and (b) a sense region that is 100% complementary to the antisense region or has mismatches at one or more positions. In one example, the molecule consists of a sense strand and an antisense strand that form a 19 base double stranded complex and mismatches that are located at positions 6, 13 or 19 of the sense region, wherein said positions are defined relative to the 5' most nucleotide of the sense strand that is part of the duplex region. For all of the descriptions relayed above, the following modifications can be adopted: sense region positions 1 and 2 and all Cs and Us have 2'-O-Me modifications, and all other 2' positions of the sense region have 2'-OH groups, and wherein all Cs and Us of the antisense region are 2'-F modified, all other nucleotides of the antisense region have 2'-OH groups, and the nucleotide at position 1 of the antisense region is phosphorylated and there is a UU overhang attached to the 3' end of the antisense region, wherein the internucleotide bond between the two nucleotides of the overhang as well as the first nucleotide of the overhang and the 3' most antisense nucleotide of the duplexed region of the antisense strand is a phosphorothioate linkage; and a cholesterol moiety is attached to the 3' end of the sense region by a C5 linker. In yet another embodiment, the siRNA has the same features as the aforementioned but the antisense strand has at least one 2'-O-Me modification instead of a 2'-F modification.

The pharmaceutically acceptable carrier may comprise one or more of excipients, such as vehicles adjuvants, pH adjusting and buffering agents, tonicity adjusting agents, stabilizers and wetting agents. Furthermore, in some embodiments, the siRNA is delivered in microcapsules, for example by coacervation techniques or by interfacial polymerization (e.g., hydroxymethylcellulose or gelatin-microcapsules and poly-(methylmethasylate) microcapsules, respectively) in colloidal drug delivery systems (for example, liposomes, microspheres, microemulsions, nano-particles, and nanocapsules or microemulsions).

The siRNA may be introduced into a cell or organism by any method that is now known or that comes to be known and that from reading this disclosure, persons skilled in the art would determine would be useful in connection with the present invention in enabling siRNA to cross the cellular membrane. These methods include, but are not limited to, any manner of transfection, such as, for example, transfection employing DEAE-Dextran, calcium phosphate, cationic lipids/liposomes, micelles, manipulation of pressure, microinjection, electroporation, immunoporation, use of vectors such as viruses, plasmids, cosmids, bacteriophages, cell fusions, and coupling of the polynucleotides to specific conjugates or ligands such as antibodies, antigens, or receptors, passive introduction, adding moieties to the siRNA that facilitate its uptake, and the like.

In another embodiment, the present invention features use of an siRNA that targets VEGFA in the manufacture of a medicament for treating, inhibiting or ameliorating one or more of the following conditions: psoriasis, cancer, rheumatoid arthritis, ocular neovascularization, abnormal angiogenesis, retinal vascular permeability, retinal edema, diabetic retinopathy (particularly proliferative diabetic retinopathy), diabetic macular edema, exudative age-related macular degeneration, sequela associated with retinal ischemia, and posterior segment neovascularization. Recipients of the siRNAs of the present invention may for example, be persons who are afflicted with one or more of the aforementioned disorders.

The dosage of the siRNA is preferably a therapeutically effective amount. A therapeutically effective amount will be determined at least in part by the age, weight and condition or severity of the affliction of the organism to be treated.

Examples of the siRNAs of the present invention may comprise an antisense sequence selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, and 88, and the corresponding sense strand in Table I.

TABLE 1 shows the silencing activities of 42 unmodified siRNAs tested in vitro as described in the Examples Section.

| Seq. Ref. | SEQ ID NO: | Top: Sense Strand, 5'→3'<br>Bottom: Antisense strand, 5'→3' | % VEGFA RNA remaining | % VEGFA Protein remaining |
|---|---|---|---|---|
| vegfa 2.1 | 1<br>2 | UACUAAAUCUCUCUCCUUU<br>AAAGGAGAGAGAUUUAGUA | 41.6 | 50.0 |
| vegfa 2.2 | 3<br>4 | ACAGAACGAUCGAUACAGA<br>UCUGUAUCGAUCGUUCUGU | 22.5 | 20.6 |
| vegfa 2.3 | 5<br>6 | CGACAGAACAGUCCUUAAU<br>AUUAAGGACUGUUCUGUCG | 19.9 | 21.2 |
| vegfa 2.4 | 7<br>8 | GAAGAGACACAUUGUUGGA<br>UCCAACAAUGUGUCUCUUC | 22.3 | 21.4 |
| vegfa 2.5 | 9<br>10 | GUCACUAGCUUAUCUUGAA<br>UUCAAGAUAAGCUAGUGAC | 13.6 | 31.6 |
| vegfa 2.6 | 11<br>12 | CAGCACACAUUCCUUUGAA<br>UUCAAAGGAAUGUGUGCUG | 57.3 | 44.4 |
| vegfa 2.9 | 13<br>14 | GGAGACCACUGGCAGAUGU<br>ACAUCUGCCAGUGGUCUCC | 24.1 | 37.5 |
| VEGFA 2.11 | 15<br>16 | GCUCGGUGCUGGAAUUUGA<br>UCAAAUUCCAGCACCGAGC | 51.0 | 35.1 |
| vegfa 2.12 | 17<br>18 | GAAAGACAGAUCACAGGUA<br>UACCUGUGAUCUGUCUUUC | 20.8 | 27.8 |
| vegfa 2.14 | 19<br>20 | CCAGAAACCUGAAAUGAAG<br>CUUCAUUUCAGGUUUCUGG | 31 | 22.5 |
| vegfa 2.15 | 21<br>22 | GAGAAGAGACACAUUGUUG<br>CAACAAUGUGUCUCUUCUC | 36.6 | 20.5 |
| vegfa 2.17 | 23<br>24 | CGACAAAGAAAUACAGAUA<br>UAUCUGUAUUUCUUUGUCG | 40.8 | 40.0 |
| vegfa 2.18 | 25<br>26 | GGGCAAAUAUGACCCAGUU<br>AACUGGGUCAUAUUUGCCC | 12.2 | 39.8 |
| vegfa 2.19 | 27<br>28 | GAAGAGAAGAGACACAUUG<br>CAAUGUGUCUCUUCUCUUC | 43.3 | 21 |
| vegfa 2.20 | 29<br>30 | GAAACCAGCAGAAAGAGGA<br>UCCUCUUUCUGCUGGUUUC | 47.6 | 44 |
| vegfa 2.21 | 31<br>32 | GAUCACAGGUACAGGGAUG<br>CAUCCCUGUACCUGUGAUC | 44.8 | 33.1 |
| vegfa 2.22 | 33<br>34 | GGAAAGAGGUAGCAAGAGC<br>GCUCUUGCUACCUCUUUCC | 52 | 53.3 |
| vegfa 2.23 | 35<br>36 | GAGAUGAGCUUCCUACAGC<br>GCUGUAGGAAGCUCAUCUC | 88.5 | 14.7 |
| vegfa 2.24 | 37<br>38 | GAUCAAACCUCACCAAGGC<br>GCCUUGGUGAGGUUUGAUC | 30.8 | 11.3 |

TABLE 1-continued shows the silencing activities of 42 unmodified siRNAs tested in vitro as described in the Examples Section.

| Seq. Ref. | SEQ ID NO: | Top: Sense Strand, 5'→3'<br>Bottom: Antisense strand, 5'→3' | % VEGFA RNA remaining | % VEGFA Protein remaining |
|---|---|---|---|---|
| Vegfa 2.25 | 39<br>40 | CAACAAAUGUGAAUGCAGA<br>UCUGCAUUCACAUUUGUUU | 22.0 | 5.52 |
| vegfa 3.1 | 41<br>42 | AAAUGAAGGAAGAGGAGAC<br>GUCUCCUCUUCCUUCAUUU | 16.2 | 9 |
| vegfa 3.2 | 43<br>44 | AAUGCAGACCAAAGAAAGA<br>UCUUUCUUUGGUCUGCAUU | 25.3 | 11.5 |
| vegfa 3.3 | 45<br>46 | ACAUAGGAGAGAUGAGCUU<br>AAGCUCAUCUCUCCUAUGU | 16.3 | 14.3 |
| vegfa 3.4 | 47<br>48 | ACGACAAAGAAAUACAGAU<br>AUCUGUAUUUCUUUGUCGU | 32.6 | 52.4 |
| vegfa 3.5 | 49<br>50 | AGACACACCCACCCACAUA<br>UAUGUGGGUGGGUGUGUCU | 17.6 | 26.1 |
| vegfa 3.6 | 51<br>52 | AGACAUUGCUAUUCUGUUU<br>AAACAGAAUAGCAAUGUCU | 31.4 | 25.7 |
| vegfa 3.7 | 53<br>54 | AGAGAAAAGAGAAAGUGUU<br>AACACUUUCUCUUUUCUCU | 23.4 | 9.8 |
| vegfa 3.8 | 55<br>56 | AGCACACAUUCCUUUGAAA<br>UUUCAAAGGAAUGUGUGCU | 26.6 | 42 |
| vegfa 3.9 | 57<br>58 | CAAAUGUGAAUGCAGACCA<br>UGGUCUGCAUUCACAUUUG | 45.8 | 35.4 |
| vegfa 3.10 | 59<br>60 | CACACAUUCCUUUGAAAUA<br>UAUUUCAAAGGAAUGUGUG | 39.3 | 28.3 |
| vegfa 3.11 | 61<br>62 | CAGAACAGUCCUUAAUCCA<br>UGGAUUAAGGACUGUUCUG | 22.9 | 34.4 |
| vegfa 3.12 | 63<br>64 | CAGAGAAAAGAGAAAGUGU<br>ACACUUUCUCUUUUCUCUG | 30.1 | 30.7 |
| vegfa 3.13 | 65<br>66 | CCAGCACAUAGGAGAGAUG<br>CAUCUCUCCUAUGUGCUGG | 34.7 | 22.3 |
| vegfa 3.16 | 67<br>68 | CGAGAUAUUCCGUAGUACA<br>UGUACUACGGAAUAUCUCG | 32.8 | 61 |
| vegfa 3.17 | 69<br>70 | CUACUGUUUAUCCGUAAUA<br>UAUUACGGAUAAACAGUAG | 40.9 | 55.2 |
| vegfa 3.18 | 71<br>72 | CUGAAAUGAAGGAAGAGGA<br>UCCUCUUCCUUCAUUUCAG | 43.5 | 43 |
| vegfa 3.19 | 73<br>74 | GAAAUGAAGGAAGAGGAGA<br>UCUCCUCUUCCUUCAUUUC | 42.7 | 48.3 |
| vegfa 3.20 | 75<br>76 | GAACAGUCCUUAAUCCAGA<br>UCUGGAUUAAGGACUGUUC | 25.9 | 30.9 |
| vegfa 3.21 | 77<br>78 | GAGAGAUGAGCUUCCUACA<br>UGUAGGAAGCUCAUCUCUC | 64.6 | 33 |
| vegfa 3.22 | 79<br>80 | GAGAUAUUCCGUAGUACAU<br>AUGUACUACGGAAUAUCUC | 60.5 | 61.3 |
| vegfa 3.23 | 81<br>82 | GAGGCAGAGAAAAGAGAAA<br>UUUCUCUUUUCUCUGCCUC | 26.9 | 32.4 |
| vegfa 3.24 | 83<br>84 | GAUAUUAACAUCACGCUCUU<br>AAGACGUGAUGUUAAUAUC | 37.8 | 73.5 |
| vegfa 3.25 | 85<br>86 | GCACACAUUCCUUUGAAAU<br>AUUUCAAAGGAAUGUGUGC | 18.8 | 38.1 |

TABLE 1-continued shows the silencing activities of 42 unmodified siRNAs tested in vitro as described in the Examples Section.

| Seq. Ref. | SEQ ID NO: | Top: Sense Strand, 5'→3'<br>Bottom: Antisense strand, 5'→3' | % VEGFA RNA remaining | % VEGFA Protein remaining |
|---|---|---|---|---|
| vegfa 3.26 | 87<br>88 | GCGGAUCAAACCUCACCAA<br>UUGGUGAGGUUUGAUCCGC | 30 | 33.5 |

TABLE 2 shows the silencing activity of a selection of siRNAs in unmodified and siStable modified formats. Specifically, data in columns D and E are derived from unmodified molecules at 24 hours. Data in columns F, G, H, and I are derived from siStable modified molecules at 72 hours. Data in columns F and G were derived when siRNA were transfected into cells at 100 nM concentrations.

| A<br>Seq.<br>Ref. | B<br>SEQ<br>ID<br>NO: | C<br>Top: Sense Strand, 5'→3'<br>Bottom: Antisense strand, 5'→3' | D<br>RNA<br>$IC_{50}$<br>(nM) | E<br>protein<br>$IC_{50}$<br>(nM) | F<br>siStable<br>% RNA<br>remaining | G<br>siStable<br>% protein<br>remaining | H<br>RNA<br>$IC_{50}$<br>(nM) | I<br>protein<br>$IC_{50}$<br>(nM) |
|---|---|---|---|---|---|---|---|---|
| vegfa 2.1 | 1<br>2 | UACUAAAUCUCUCUCCUUU<br>AAAGGAGAGAGAUUUAGUA | 0.31 | 0.51 | 17 | 41 | 4.78 | 2.35 |
| vegfa 3.1 | 41<br>42 | AAAUGAAGGAAGAGGAGAC<br>GUCUCCUCUUCCUUCAUUU | 5.2 | 0.82 | 18 | 12 | 0.36 | 0.15 |
| vegfa 3.2 | 43<br>44 | AAUGCAGACCAAAGAAAGA<br>UCUUUCUUUGGUCUGCAUU | 0.93 | 0.17 | 10 | 9 | 0.4 | 0.37 |
| vegfa 3.3 | 45<br>46 | ACAUAGGAGAGAUGAGCUU<br>AAGCUCAUCUCUCCUAUGU | 0.43 | 0.59 | 11 | 10 | 0.82 | 0.77 |
| vegfa 3.6 | 51<br>52 | AGACAUUGCUAUUCUGUUU<br>AAACAGAAUAGCAAUGUCU | 0.81 | 0.94 | 28 | 31 | 23 | 3.17 |
| vegfa 3.7 | 53<br>54 | AGAGAAAAGAGAAAGUGUU<br>AACACUUUCUCUUUUCUCU | 1.3 | 0.46 | 10 | 10 | 0.26 | 0.46 |
| vegfa 3.10 | 59<br>60 | CACACAUUCCUUUGAAAUA<br>UAUUUCAAAGGAAUGUGUG | 1.05 | 0.97 | 13 | 20 | 0.26 | 0.17 |
| vegfa 3.12 | 63<br>64 | CAGAGAAAAGAGAAAGUGU<br>ACACUUUCUCUUUUCUCUG | 4.6 | 1 | 10 | 15 | 0.11 | 0.21 |
| vegfa 3.20 | 75<br>76 | GAACAGUCCUUAAUCCAGA<br>UCUGGAUUAAGGACUGUUC | 2 | 0.62 | 9 | 28 | 0.31 | 0.53 |
| vegfa 3.23 | 81<br>82 | GAGGCAGAGAAAAGAGAAA<br>UUUCUCUUUUCUCUGCCUC | 1.4 | 1.2 | 14 | 45 | 2.2 | 2.7 |

It is noted that the above recited duplexes do not contain mismatches. The present invention includes the specifically recited siRNAs as well as pharmaceutical compositions that contain them and methods for using them. The present invention also includes siRNAs that are similar to them but have a different base at position 6 or position 13 or position 19 of the sense strand or at both positions 6 and 13 or both of positions 13 and 19 or at both of positions 6 and 19 of the sense strand or at all three of positions, 6, 13 and 19 of the sense strand. Thus at any of those three positions, wherein in tables 1 or 2 there is an A complementary to a U, a U, C or G may be inserted, wherein in tables 1 or 2 there is an U complementary to an A, an A, C or G may be inserted, wherein in tables 1 or 2 there is a C complementary to a G, a U, A or G may be inserted, wherein in tables 1 or 2 there is a G complementary to a C, a U, C or A may be inserted. Still further, any of these siRNAs may contain overhang regions, e.g., a UU 3' antisense overhang and/or a UU 3' sense overhang.

By way of further example, in one embodiment, the present invention is directed to an siRNA from Table 2, or to an siRNA that differs from that of table 2 in that the sense strand has three mismatched nucleotides that are located at positions, 6, 13, and 19 with the opposite nucleotides on the antisense e.g., an siRNA that contains the sense and antisense sequences of vegfa 3.7, except that the sense strand has three mismatched nucleotides that are located at positions, 6, 13, and 19. In some embodiments the mismatches are selected such that one or more, for example, two or three of the mismatched bases are the same as the bases on the opposite strand and no other mismatched bases are present in the duplex. By way of a non-limiting example, for vegfa 3.7 a duplex may be SS- 5' AGAGAUAAGAGAUAGUGUA 3' (SEQ ID No: 91)

AS- 3' UCUCUUUUCUCUUUCACAA 5' (SEQ ID No: 54)

This duplex, as well as any other duplex disclosed herein, may contain 3' overhangs on either the sense strand or the antisense strand. By way of a non-limiting example, there may be a dinucleotide overhangs, e.g., UU. This overhang may exist on the sense strand, but not the antisense strand; on the antisense strand but not the sense strand; on both strands or on neither strand. Each overhang may be constructed to have a standard internucleotide linkage between nucleotides of the overhang and a standard linkage to the 3' end of the appropriate strand of the duplex, or in the overhang, the bond between the two nucleotides of the overhang as well as the first nucleotide of the overhang and the 3' most antisense nucleotide of the duplexed region of the strand is a phosphorothioate linkage. Thus, e.g., in the vegfa 3.7 duplex of the preceding paragraph, SEQ ID No: 54 may contain a UU 3' antisense overhang that does not contain a phosphorothioate linkage between the nucleotides of the overhang or between the overhang and the 3' of SEQ ID No: 54, or there may be phosphorothioate linkages at one or both of those positions.

Unless otherwise specified, each of the features of each of the aforementioned embodiments may be used in connection with any of the other embodiments, unless such use is incompatible or inconsistent with that embodiment.

Having described the invention with a degree of particularity, examples will now be provided. These examples are not intended to and should not be construed to limit the scope of the claims in any way.

EXAMPLES

Example 1

General Techniques for In Vitro Studies siRNA Selection for Study

A collection of siRNAs capable of targeting all the variants of VEGFA were identified (NM_001025366, NM_003376, NM_001025367, NM_001025368, NM_001033756, NM_001025369, NM_001025370). Table 1 provides a list of the siRNAs along with the sense and antisense strand sequences (5'→3').

To assess the relative functionality of each siRNA, sequences were synthesized using 2' ACE chemistry (U.S. Pat. No. 6,008,400; U.S. Pat. No. 6,111,086; U.S. Pat. No. 6,590,093; Scaringe (2000) *Methods in Enzymology* 317:3-18; Scaringe (2001) *Methods* 23(3):206-217) and then transfected into HeLa cells (ATCC, #CCL-2) by lipid mediated transfection using the manufacturer's protocols (10,000 cells per well in a 96 well format, 100 nM siRNA, 0.2 µl DharmaFECT 1/well). Seventy-two hours post-transfection, overall cell viability and target knockdown at the mRNA and protein level was determined. All assays were performed in triplicate and for a select group of siRNAs, a dose curve (0.001, 0.01, 0.1, 1.0, 10.0, and 100 nM) was performed to ascertain the $IC_{50}$ for the siRNA/target mRNA pair. Positive and negative controls were included in all experiments and consisted of a non-targeting control (NTC #5 sense strand sequence: 5'-UGGUUUACAUGUCGACUAAUU-3' (SEQ ID NO: 89)) and a positive control targeting PPIB (sense strand sequence: 5'-ACAGCAAAUUCCAUCGUGU-3' (SEQ ID NO: 90)). Note: the positive control molecule used in these studies contains the following modifications: sense strand contains a 2'-O-methyl modification on the first two nucleotides counting from the 5' end of the strand; antisense strand contains a 5' phosphate group; both sense and antisense strands contain a 2 nucleotide UU overhang on the 3' end.

Target mRNA and Protein Knockdown Analysis

Target mRNA knockdown was determined at 72 hour post-transfection using the branched DNA assay (QuantiGene Screen Kit, Panomics). The expression of PPIB was used as a reference mRNA and the targeted mRNA knockdown was further normalized to the corresponding non-targeting control (NTC). Protein expression was assessed by performing a VEGFA ELISA assay on supernatants from transfected cells at 72 hours post-transfection. The ELISA was performed according to the manufacturer's instructions using 50 µL of supernatant (Human VEGFA ELISA kit, Thermo Scientific). Absorbance was read on a spectrophotometer at 450 nM. Data was normalized to the corresponding NTC control.

Cell Viability Assay

Cell viability was assessed by a resazurin assay at 72 hours post-transfection. Resazurin was added directly into the culture media and the plates were incubated for 1-1.5 hours prior to measuring the fluorescence on a Wallac VICTOR 2 (Perkin Elmer Life Sciences) plate reader (Excitation 530 nm, Emission 590 nm and 1 second exposure). Data was normalized to the corresponding NTC control.

siRNA Designs for Study siRNA configurations tested in the in vitro studies include (1) the standard unmodified design (19 base pairs duplex, UU overhangs on the 3' end of both sense and antisense strands), and (2) the stabilized design (a 19 base pair duplex; sense strand modifications: 2'-O-methyl modifications on nucleotides 1 and 2 (counting from the 5' end of the strand) plus 2'-O-methyl modifications on all Cs and Us; antisense strand modifications: a phosphate on the 5' terminal nucleotide, 2' F modifications on all Cs and Us, a 2 nucleotide (UU) overhang on the 3' terminus, and a phosphorothioate internucleotide modification between the two nucleotides of the overhang and between the first (3' most) nucleotide of the duplex and the first nucleotide of the overhang).

For in vivo studies, siRNAs included the following design:
a 19 bp duplex
sense strand modifications
   2'-O-methyl modifications on nucleotides 1 and 2 (counting from the 5' end of the strand)
   2'-O-methyl modifications on all Cs and Us
   cholesterol conjugated to the 3' terminus using a C5 linker (see U.S. Pat. Pub. 2009/0209626, published Aug. 20, 2009 the disclosure of which is incorporated by reference as if set forth fully herein)
antisense strand modifications
   5' phosphate
   2' F on all Cs and Us
   a two nucleotide (UU) overhang on the 3' terminus
   phosphorothioate internucleotide modifications between the two nucleotides of the overhang and between the first (3' most) nucleotide of the duplex and the first nucleotide of the overhang.

In addition, mismatches at positions 6, 13, and 19 have been incorporated into molecules used in in vivo studies. In all cases, mismatches between the two strands of the siRNA are achieved by changing the nucleotide of the sense strand to have identity with the base (on the antisense strand) that typically pairs with that position. Thus, for instance, if the sense-antisense pair at sense strand position 6 is normally U-A, then the mismatch will be introduced by converting the pair to A-A. Similarly, if the sense-antisense pair at sense strand position 6 is G-C, then the mismatch will be C—C. In this way, a mismatch is incorporated into the duplex, but the antisense strand remains the reverse complement of the intended target.

Example 2

Results of In Vitro and In Vivo Studies

The performance of all the sequences tested in vitro is shown in Table 1. Multiple sequences were observed to provide greater than 70% gene knockdown at both the RNA and protein level including, for instance, Vegfa 2.2, 2.3, 2.4, 2.12, 3.1, 3.2, 3.3, 3.5, and 3.7. In addition, when a subset of the collection was tested with the stabilized design, overall performance was found to be equivalent or better than that observed in the unmodified state (see, for instance, vegfa 2.1, 3.2, 3.3). As Table 2 shows, in both the unmodified and modified states, $IC_{50}$ for RNA knockdown ranged from approximately 0.11→23 nM while $IC_{50}$ for protein knockdown ranged from ~0.17→3.17 nM. Based on these results, two sequences, Vegfa 3.2 and 3.7, were re-synthesized using the in vivo design (referred to as "Accell") described previously. The results of these experiments may be further demonstrated by reference to the accompanying figures.

Figure 1B:
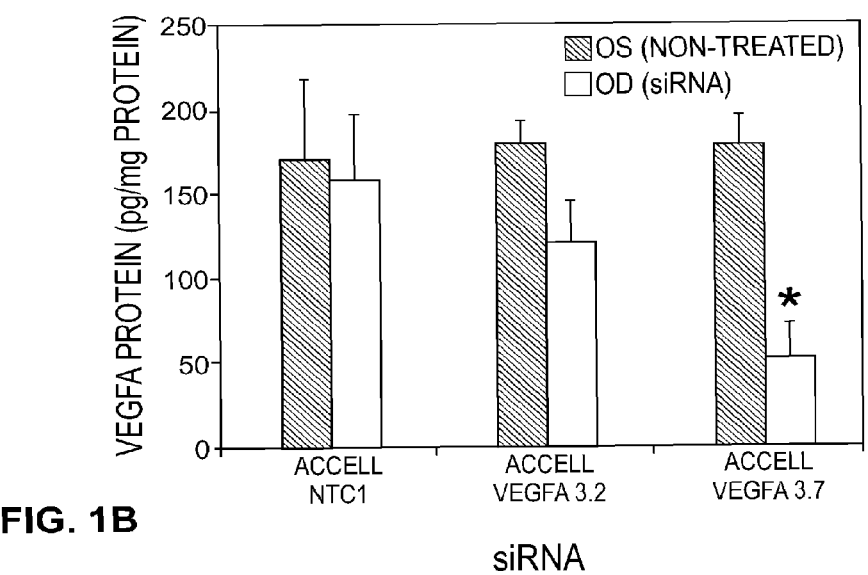

FIGS. 1A and 1B illustrate the effect of intravitreal (IVT) injection of Accell VEGFA siRNAs on expression of VEGFA mRNA and protein, respectively, in the rat retina at 72 h post-injection. Lewis rats received 10 μg IVT injections (OD) of Accell VEGFA 3.2, Accell VEGFA 3.7 or Accell non-targeting control #1 (NTC1) siRNAs resuspended in 1× siRNA buffer (Dharmacon). The Accell NTC1 siRNA sense strand sequence is 5'-UGGUUAACAUGUCGACUAA-3' (SEQ ID NO: 92); the Accell NTC1 siRNA antisense strand sequence is 5'-UUAGUCGACAUGUAAACCAUU-3' (SEQ ID NO: 93). Contralateral eyes (OS) were not treated. Eyes were harvested at 72 h post-injection, and retinas were isolated by dissection. (1A) Total RNA was extracted using Trizol (Invitrogen), and VEGFA and β-actin (ACTB) mRNA levels were determined by Taqman qRT-PCR assay (Applied Biosystems). VEGFA mRNA expression was normalized to β-actin expression. (1B) Protein was extracted using RIPA buffer (Pierce), and rat VEGFA protein level was determined by ELISA (R&D Systems). VEGFA protein expression was normalized to total protein determined by BCA assay (Pierce). Data are presented as the mean (n=6)±standard deviation (error bars). *, P<0.001 versus NTC1. Both of the VEGFA siRNAs significantly reduced the expression of VEGFA mRNA; VEGFA 3.7 also significantly reduced VEGFA and protein. The NTC1 control siRNA had little, if any, effect on VEGFA expression.

Figure 2:
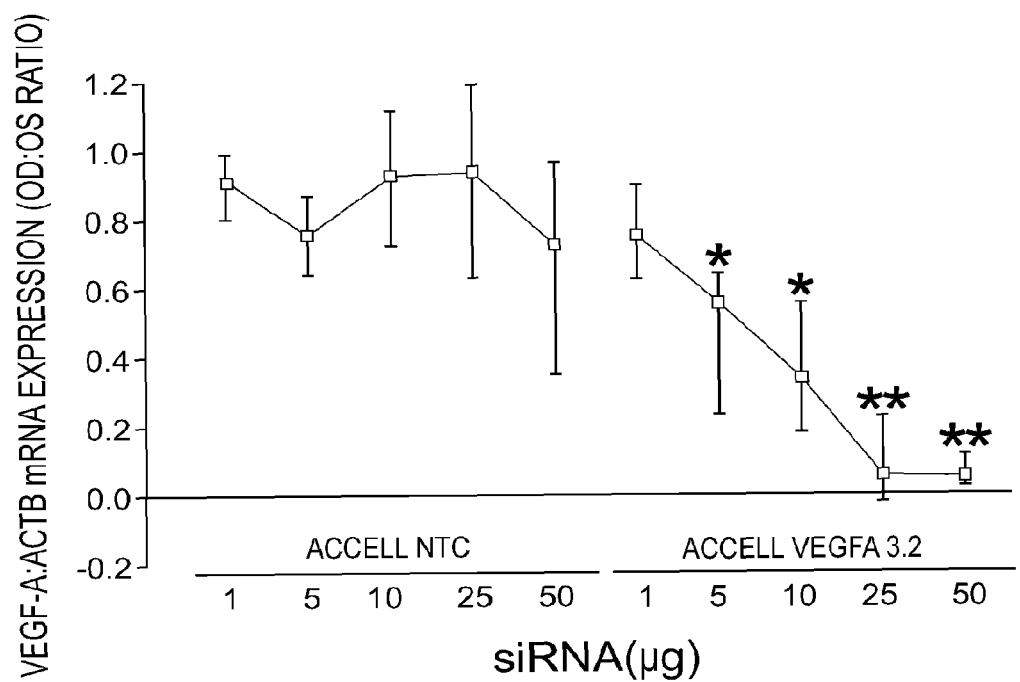
FIG. 2 is a representation of a dose response curve for an siRNA, VEGFA 3.2 (modified as an Accell molecule).

FIG. 2 shows a comparison between the dose response curves for Accell VEGFA 3.2 siRNA and a control siRNA in the rat retina. Lewis rats received 1-25 μg IVT injections (OD) of Accell VEGFA 3.2 or Accell NTC1 control siRNAs resuspended in 1× siRNA buffer (Dharmacon). Contralateral eyes (OS) were not treated. Eyes were harvested at 72 h post-injection, and retinas were isolated by dissection. Total RNA was extracted using Trizol Plus (Invitrogen), and VEGFA and β-actin mRNA levels were determined by Taqman qRT-PCR assay (Applied Biosystems). VEGFA mRNA expression was normalized to β-actin mRNA. Data are presented as the mean OD:OS ratio (ratio of VEGFA level in the treated eye versus the non-treated eye) for normalized VEGFA mRNA expression (n=6)±standard deviation (error bars). *, P<0.05; **, P<0.01 versus Accell NTC1. Intravitreal injection of increasing amounts of Accell VEGFA siRNA 3.2 resulted in a dose response that reached essentially complete silencing of VEGFA mRNA expression at 25 μg.

Figure 3A:
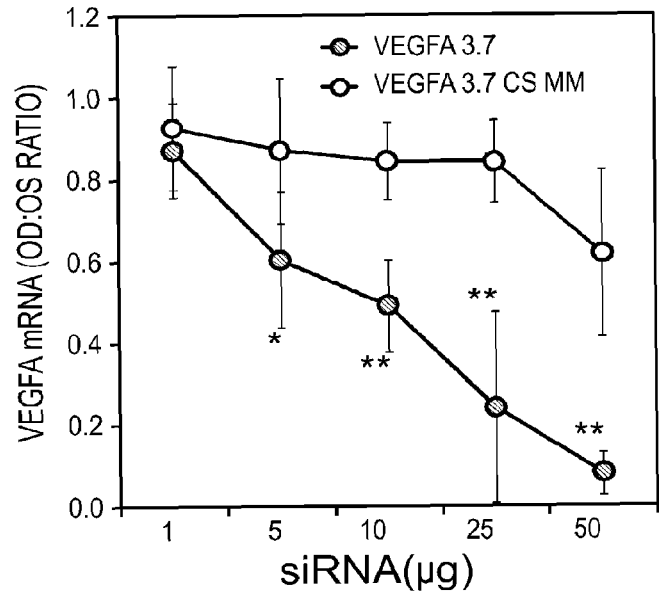
FIGS. 3A and 3B are representations of dose response curves for another siRNA, VEGFA 3.7 (modified as an Accell molecule).
Figure 3B:
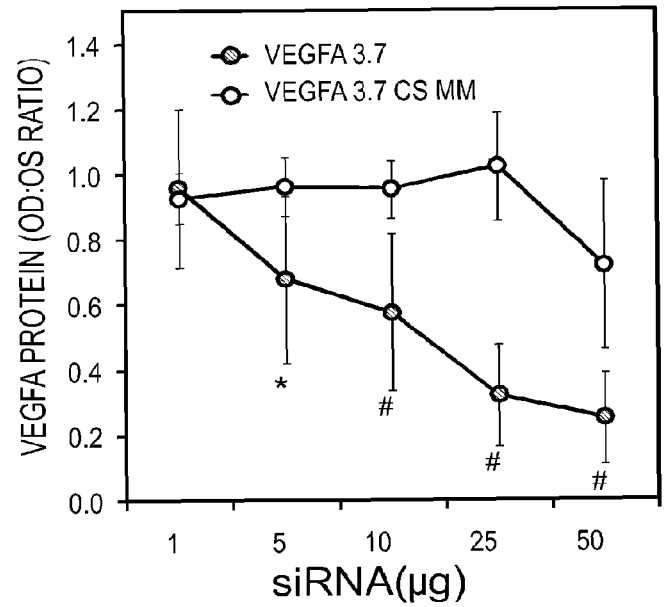

FIGS. 3A and 3B shows a comparison between the dose response curves for Accell VEGFA 3.7 siRNA and a control siRNA in the rat retina. Lewis rats received 1-50 μg IVT injections (OD) of Accell VEGFA 3.7 siRNA or Accell VEGFA 3.7 cleavage site mismatch (CS MM) control siRNAs resuspended in 1× siRNA buffer (Dharmacon). The Accell VEGFA 3.7 CS MM control siRNA has the same sequence as Accell VEGFA 3.7 siRNA except for a 3-nucleotide mismatch to the VEGFA mRNA target sequence. The Accell VEGFA 3.7 CS MM siRNA sense strand sequence is 5'-AGAGAUAACUCAUAGUGUA-3' (SEQ ID NO: 94); the Accell VEGFA 3.7 CS MM siRNA antisense strand sequence is 5'-AACACUUUGAGUUUCUCUUU-3' (SEQ ID NO: 95). Contralateral eyes (OS) were not treated. Eyes were harvested at 72 h post-injection, and retinas were isolated by dissection. (3A) Total RNA was extracted using Trizol (Invitrogen), and VEGFA and β-actin mRNA levels were determined by Taqman qRT-PCR assay (Applied Biosystems). VEGFA mRNA expression was normalized to β-actin mRNA expression. (3B) Protein was extracted using RIPA buffer (Pierce), and rat VEGF-A level was determined by ELISA (R&D Systems). VEGFA protein expression was normalized to total protein level determined by BCA assay (Pierce). Data are presented as the mean OD:OS ratio for normalized VEGFA mRNA or protein expression (n=6)±standard deviation (error bars). *, P<0.03; **, P<0.0002; #, P<0.005. Intravitreal injection Accell VEGFA 3.7 siRNA at doses as low as 5 μg caused a significant reduction in VEGFA expression at both the mRNA and protein levels. The Accell VEGFA 3.7 siRNA exhibited a dose response that reached >70% inhibition of VEGFA mRNA expression and approximately 80% inhibition of VEGFA protein expression at 25 μg siRNA. Non-RNAi-mediated inhibition of VEGFA expression was also observed with the control siRNA. This effect was less pronounced for VEGFA protein than for VEGFA mRNA.

Figure 4A:
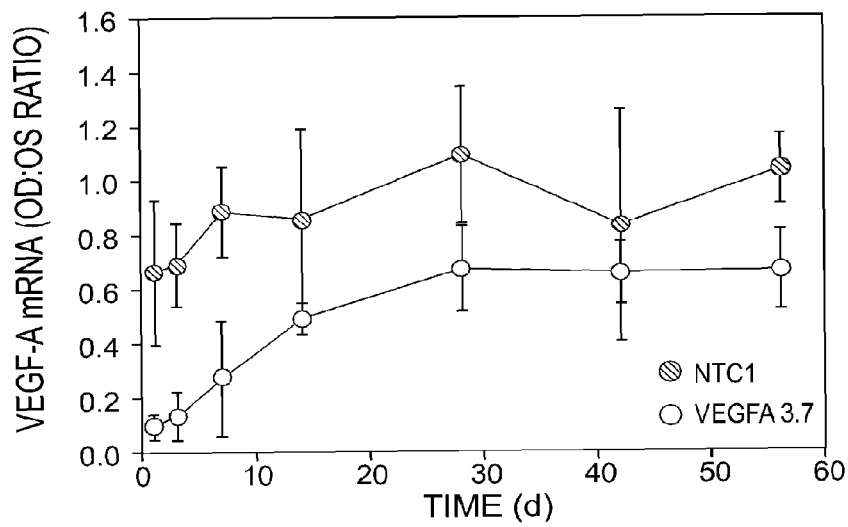
FIGS. 4A and 4B demonstrate a duration of action of up to eight weeks for an siRNA, VEGFA 3.7, modified as an Accell molecule and delivered by IVT injection in rats.
Figure 4B:
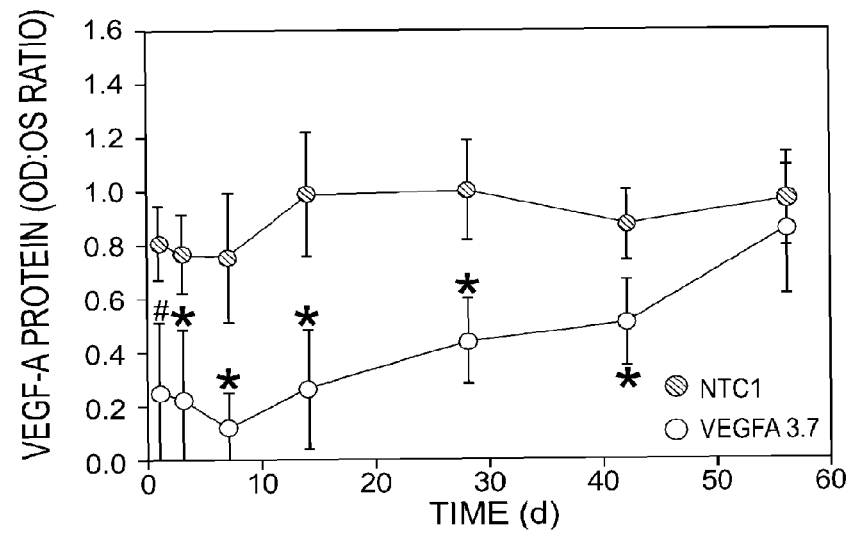

FIGS. 4A and 4B show the time duration of action for the Accell VEGFA 3.7 siRNA. Lewis rats received 25 μg IVT injections (OD) of Accell VEGFA 3.7 siRNA or Accell NTC1 control siRNAs resuspended in 1× siRNA buffer (Dharmacon). Contralateral eyes (OS) were not treated. Eyes were harvested at 1, 3, 7, 14, 28, 42, and 56 d post-injection, and retinas were isolated by dissection. Expression of VEGFA mRNA (4A) and VEGFA protein (4B) was evaluated as described in the previous examples. Data are presented as the mean OD:OS ratio for normalized VEGFA mRNA or protein expression (n=6)±standard deviation (error bars). *, P<0.001; #, P<0.002 versus NTC1. Intravitreal injection of Accell VEGFA 3.7 siRNA caused significant inhibition of VEGFA mRNA and protein expression within 24 h. Inhibition persisted for several weeks.

Figure 5A:
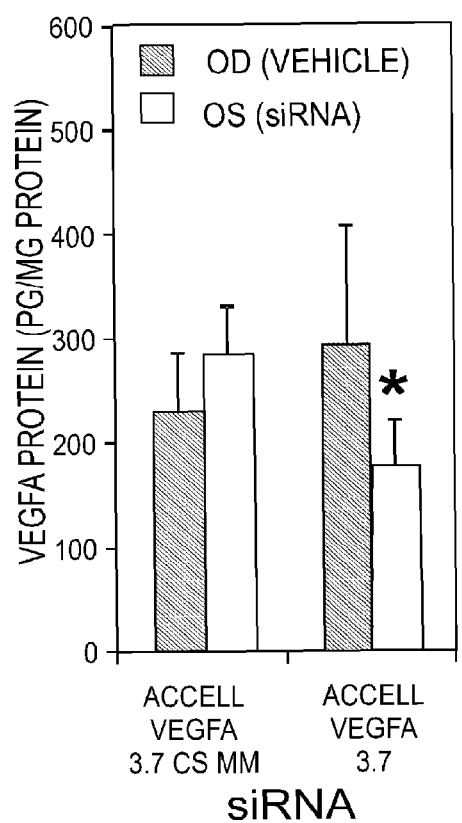
FIGS. 5A and 5B demonstrate inhibition of VEGFA expression and preretinal neovascularization in the rat oxygen-induced retinopathy (OIR) model by siRNA, VEGFA 3.7, modified as an Accell molecule.
Figure 5B:
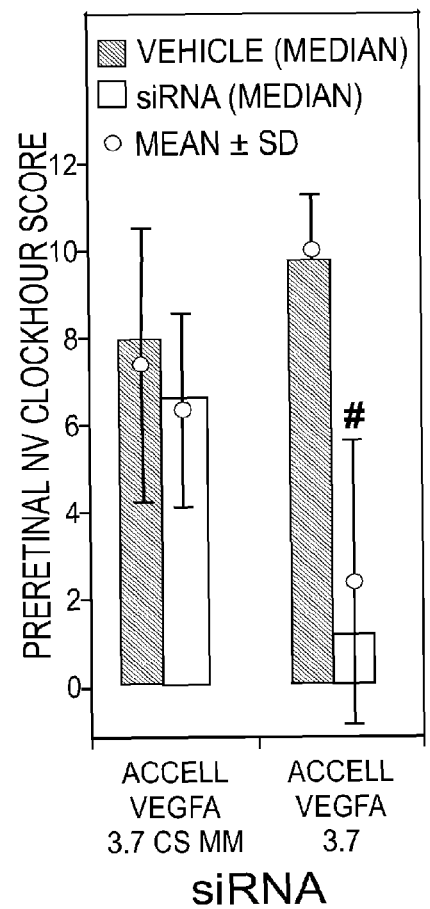

FIGS. 5A and 5B show inhibition of VEGFA protein expression and preretinal neovascularization, respectively, in the rat oxygen-induced retinopathy (OIR) model (modified from Penn et al., *Pediatr. Res.* 36:724-731, 1994). Following 14 d of cycling between 50% and 10% $O_2$, neonatal Sprague Dawley rats were exposed to room air (21% $O_2$) for 7 d (postpartum days 15-21, P15-P21). On days P15 and P18, animals received 25 μg IVT injections (OS) of Accell VEGFA siRNA 3.7 or Accell VEGFA 3.7 CS MM control siRNA resuspended in 1× siRNA buffer (Dharmacon). Contralateral eyes (OD) were treated with vehicle (1× siRNA buffer). Injection volume was 1 μl. Eyes were harvested on day P21, and retinas were isolated by dissection. (5A) Protein was extracted using RIPA buffer (Pierce), and VEGFA protein level was determined by ELISA (R&D Systems). VEGFA protein expression was normalized to total protein level determined by BCA assay (Pierce). Data are presented as mean normalized VEGFA protein expression (n=7)±standard deviation (error bars). *, P<0.03. (5B) Retinas were fixed in 10% neutral buffered formalin for 24 h, subjected to ADPase staining, and fixed onto slides as whole mounts. Images were acquired using a Nikon Coolscope®, and each of 12 sectors per retina was assessed for the presence or absence of neovascularization to obtain a clockhour score (n=6-8). #, P<0.05. The Accell VEGFA 3.7 siRNA caused a significant reduction in VEGFA protein expression (~40%), resulting in an approximately 88% inhibition of preretinal neovascularization. The Accell VEGFA 3.7 CS MINI control siRNA did not have a significant effect on either VEGFA expression or neovascularization.

As persons of ordinary skill in the art are aware, extrapolating to humans, observations made in rats is well-known.

We claim:

1. A pharmaceutical composition comprising a therapeutically effective amount of an siRNA, wherein the siRNA consists essentially of:
    (a) an antisense strand that is nineteen to thirty-six bases in length and that has a sequence that comprises SEQ ID NO: 54; and
    (b) a sense strand that is nineteen to thirty-six bases in length, wherein the antisense strand and the sense strand form a duplex region of seventeen to thirty base pairs and within the duplex region are at least 75% complementary.

2. A pharmaceutical composition comprising a therapeutically effective amount of an siRNA, wherein the siRNA comprises:
    (a) an antisense strand that is nineteen to thirty-six bases in length and that has a sequence that comprises SEQ ID NO: 54; and
    (b) a sense strand that is nineteen to thirty-six bases in length, wherein the antisense strand and the sense strand form a duplex region of seventeen to thirty base pairs and within the duplex region are at least 75% complementary, and within the duplex region, there are mismatches at one or more of positions 6, 13, or 19, wherein said positions are defined relative to the 5' end of the sense strand.

3. The pharmaceutical composition of claim 2, wherein within the sense strand positions 1 and 2 and all Cs and Us have 2'-OMe modifications, and all other positions of the sense strand have 2'—OH groups, and wherein all Cs and Us of the antisense strand have 2'-F modifications, and all other nucleotides of the antisense strand have 2'—OH groups, and the nucleotide at position 1 of the antisense strand is phosphorylated.

4. The pharmaceutical composition of claim 3, wherein the sense strand is nineteen bases in length and the antisense strand is twenty-one bases in length and the two 3' most bases of the antisense strand are a UU overhang.

5. The pharmaceutical composition of claim 4, wherein a cholesterol moiety is attached to the 3' end of the sense strand by a C5 linker.

* * * * *